US005552550A

United States Patent [19]
Bringmann et al.

[11] Patent Number: 5,552,550
[45] Date of Patent: Sep. 3, 1996

[54] MONOMERIC NAPHTHYLISOQUINOLINE ALKALOIDS AND SYNTHESIS METHODS THEREOF

[75] Inventors: Gerhard Bringmann; Roland Götz, both of Wurzburg, Germany; Michael R. Boyd, Ijamsville, Md.

[73] Assignee: The United States of America, as represented by the Department of Health and Human Services, Washington, D.C.

[21] Appl. No.: 279,291

[22] Filed: Jul. 22, 1994

[51] Int. Cl.$^6$ ................................................. C07D 217/02
[52] U.S. Cl. ........................... 546/146; 546/141; 546/149
[58] Field of Search ................................... 546/146, 149, 546/141

[56] References Cited

U.S. PATENT DOCUMENTS

| | | | |
|---|---|---|---|
| 5,260,315 | 11/1993 | Bringmann et al. | 514/307 |
| 5,409,938 | 4/1995 | Boyd | 546/150 |

FOREIGN PATENT DOCUMENTS

WO92/18125  10/1992  WIPO .................................... 546/150

OTHER PUBLICATIONS

Fleischhauer et al., "Messung und Berechnung der CD-Spektren der Biaryl-Alkaloide Ancistrocladein und Dioncophyllein A," *Z. Naturforsch,* 48b, 140–148 (1993).

Bringmann et al., "First total synthesis of korupensamines A and B," *Heterocycles,* 39(2), 503–508 (1994).

Bringmann et al., "Biomimetic oxidative dimerization of korupensamine A: Completion of the first total synthesis of michellamines A, B, and C," *Tetrahedron,* 50(32), 9643–9648 (1994).

Hoye et al., "Total synthesis of michellamines A–C: Important anti–HIV agents," *Tetrahedron Letters,* 35(47), 8747–8750 (1994).

Kelly et al., "Convergent total synthesis of the michellamines," *Tetrahedron Letters,* 35(41), 7621–7624 (1994).

Manfredi et al., "Novel alkaloids from the tropical plant *Ancistrocladus abbreviatus* inhibit cell killing by HIV–1 and HIV–2," *Journal of Med. Chem.,* 34(12), 3402–3405 (1991).

Boyd et al., "Anti–HIV Michellamines from *Ancistrocladus korupensis,*" *J. Medicinal Chemistry,* 37(12), 1740–1745 (1994).

Bringmann, *The Alkaloids,* 29 (Brossi, ed.), Academic Press, New York, 1986, pp. 141–184.

Bringmann et al., "Regioselective and Atropoisomeric–Selective Aryl Coupling to Give Naphthyl Isoquinoline Alkaloids: The First Total Synthesis of (−)-Ancistrocladine," *Angew. Chem. Int. Ed. Engl.,* 25(10), 913–915 (1986).

Bringmann et al., "Atropdiastereoselective Ring Opening of Bridged, Axial–Prostereogenic Biaryls: Directed Synthesis of (+)-Ancistrocladisine," *Angew. Chem. Int. Ed. Engl.,* 28(12), 1672–1673 (1989).

Bringmann et al., "Chiral Economy with Respect to Rotational Isomerism: Rational Synthesis of Hamatine and (Optionally) Ancistrocladine from Joint Helical Precursors," *Heterocycles,* 28(1), 137–142 (1989).

Bringmann et al., "The Synthesis of All Possible Isomeric 6,8–Dioxygenated 1,3–Dimethyl–1,2,3,4–tetrahydroisoquinoline Methyl Ethers–Useful Chiral Building Blocks for Naphthylisoquinoline Alkaloids," *Liebigs Ann. Chem,* 877–888 (1993).

Bringmann et al., "Atrop–diastereomer Separation by Racemate Resolution Techniques: N–Methyl–Dioncophylline A and its 7–Epimer from *Ancistrocladus abbreviatus,*" *Phytochemistry,* 30(4), 1307–1310 (1911).

Bringmann et al., "Dioncopeltine A and Dioncolactone A: Alkaloids from *Triphyophyllum peltatum,*" *Phytochemistry,* 30(5), 1691–1696 (1991).

Bringmann et al., "Dioncophylline B, A Naphthylisoquinoline Alkaloid with A New Coupling Type from *Triphyophyllum peltatum,*" *Phytochemistry,* 30(11), 3845–3847 (1991).

Bringmann et al., "Ancistrobrevine B, The First Naphthylisoquinoline Alkaloid with a 5,8'-Coupling Site, and Related Compounds from *Ancistrocladus abbreviatus,*" *Phytochemistry,* 31(11), 4011–4014 (1992).

Bringmann et al., "(±)-Dioncophyllacine A, A Naphthylisoquinoline Alkaloid with a 4–Methoxy Substituent from the Leaves of *Triphyophyllum peltatum,*" *Phytochemistry,* 31(11), 4015–4108 (1992).

Bringmann et al., "Dioncophylline C from the Roots of *Triphyophyllum peltatum,* the First 5,1'-Coupled Dioncophyllaceae Alkaloid," *Phytochemistry,* 31(11), 4019–4024 (1992).

Bringmann et al., "On the Biosynthesis of Acetogenic Tetrahydroisoquinoline Alkaloids: First In Vivo Feeding Experiments," *Planta Med.,* 57 (Suppl. 2), A98 (1991).

Bringmann et al., "Ancistrobrevine D: An Unusual Alkaloid from *Ancistrocladus Abbreviatus,*" *Planta Med.,* 58 (Suppl. 1), A703–704 (1992).

Bringmann et al., "A New Atropisomeric Dioncophylline A Derivative from *Triphyophyllum peltatum,*" *Planta Med.,* 59 (Suppl.), A621–622 (1993).

Bringmann et al., "The Cultivation of Tropical Lianas of the Genus *Ancistrocladus,*" *Planta Med.,* 59 (Suppl.), A623–624 (1993).

Bringmann et al., "Improved Methods for Dehydration and Hydroxy/Halogen Exchange Using Novel Combinations of Triphenylphoshine and Halogenated Ethanes," *Synthesis,* 139–141 (1983).

Bringmann et al., "Stereocontrolled Ring Opening of Axially Prostereogenic Biarly Lactones with Hydrogen Nucleo (List continued on next page.)

*Primary Examiner*—Zinna Northington Davis
*Attorney, Agent, or Firm*—Leydig, Voit & Mayer, Ltd.

[57] ABSTRACT

The present invention provides methods of preparing monomeric naphthylisoquinoline alkaloids, including the antiparasitic korupensamines and related compounds, as well as non-korupensamines and other monomeric naphthylisoquinoline alkaloids. The invention also provides new, medically useful naphthylisoquinoline compounds and derivatives thereof.

22 Claims, 10 Drawing Sheets

OTHER PUBLICATIONS philes: Directed Synthesis of a Dioncophylline A Precursor and (Optionally) its Atropdiastereomer," *Synthesis*, 825–827 (1991).

Bringmann et al., "On the Stucture of the Dioncophyllaceae Alkaloids Dioncophylline A ('Triphyophylline') and 'O–Methyl—Triphyophylline,'" *Tetrahedron Letters*, 31 (5), 639–642 (1990).

Bringmann et al., "First Total Synthesis of (–) –Dioncophylline A ('Triphyophylline') and of Selected Stereoisomers: Complete (Revised) Stereostructure," *Tetrahedron Letters*, 31(5), 643–646 (1990).

François et al., "Activity of Extracts and Naphthylisoquinoline Alkaloids from *Triphyophyllum peltatum, Ancistrocladus abbreviatus* and *A. barteri* aganist *Plasmodium falciparum* In Vitro," Phytochemistry, 35(6), 1461–1464 (1994).

Handford et al., "Syntheses of Eleutherolic Acid," *J. Chem. Soc.*, 3896–3897 (1963).

Owton et al., "tert–Butyl–3–Carboxyethyl–3–Phosphonodiethylpropionate. A Novel Reagent for Stobbe–like Condensations," *Synthtic Communications*, 23 (15), 2119–2125 (1993).

Rizzacasa et al., "Synthetic Approaches to the Alkaloids of the Ancistrocladacea: Dehydroancistrocladisine," *J. Chem. Soc.*, 301–302 (1989).

Thomas et al., "*Ancistrocladus korupensis* (Ancistrocladaceae): A New Species of Liana from Cameroon," *Novon*, 3(4), 494–498 (1993).

N-FORMYL-DIONCOPHYLLINE C

N-FORMYL-8-O-BENZYL-DIONCOPHYLLINE C

N-FORMYL-8-O-METHYL-DIONCOPHYLLINE C

N-FORMYL-8-O-PIVALOYL-DIONCOPHYLLINE C

N-FORMYL-8-O-ACETYL-DIONCOPHYLLINE C

N-FORMYL-8-O-BENZOYL-
DIONCOPHYLLINE C

8-O-METHYL-
DIONCOPHYLLINE C

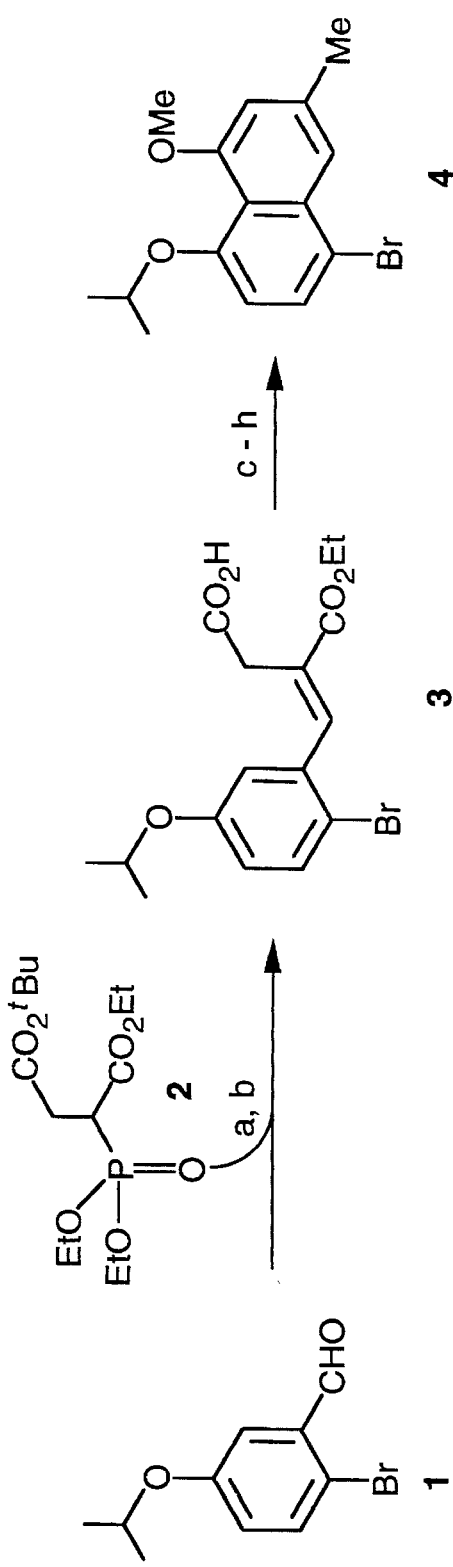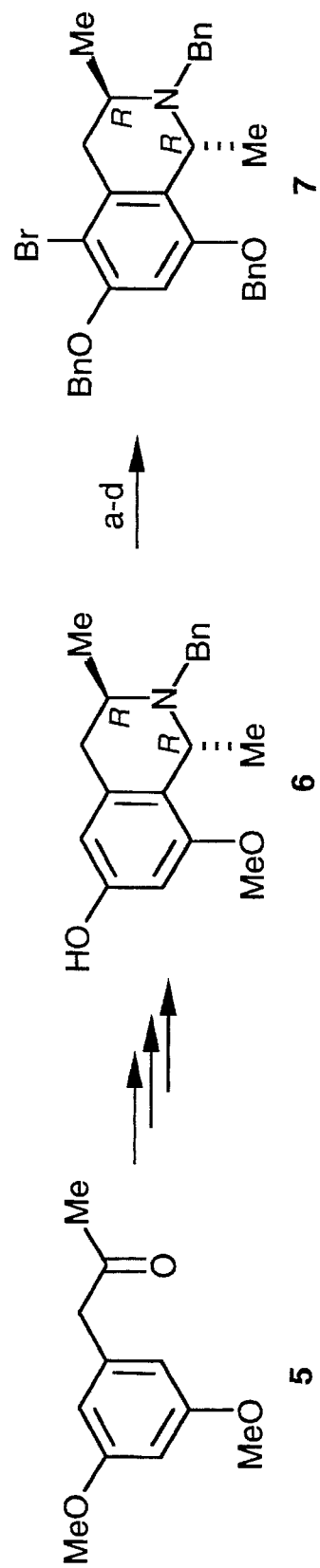
FIG. 2
FIG. 3

5,552,550

MONOMERIC NAPHTHYLISOQUINOLINE ALKALOIDS AND SYNTHESIS METHODS THEREOF

TECHNICAL FIELD OF THE INVENTION

The present invention relates to methods of preparing known and new monomeric naphthylisoquinoline alkaloids. The present invention also relates to new monomeric naphthylisoquinoline alkaloids and derivatives thereof.

BACKGROUND OF THE INVENTION

Novel, medically useful antiparasitic compounds known as korupensamines have recently been described (Hallock et al., *J. Org. Chem.*, 59, 6349-6355, 1994; Bringmann et al., *Heterocycles*, 39, 503–512, 1994; Boyd et al., U.S. Pat. No. 5,409,938). Korupensamines are members of a general chemical class of compounds known as monomeric naphthylisoquinoline alkaloids (Bringmann, *The Alkaloids*, Vol. 29 (Brossi, ed.), Academic Press, New York, 1986, pp. 141–184) which are characterized in part by their possession of a C-8' to C-5 naphthalene/isoquinoline linkage.

A method of chemically synthesizing korupensamines and related C-8' to C-5 linked naphthylisoquinoline alkaloids has heretofore been unknown. This is significant because the only known natural source of any korupensamine is the rare tropical vine *Ancistrocladus korupensis* of Central Africa (Thomas and Gereau, *Novon*, 3, 494–498, 1993; Hallock et al., 1994, supra). This lack of any synthetic access to korupensamines undoubtedly has been a critical hindrance to the medical use of the compounds, and to the exploration of alternative medical uses as well.

In addition to the korupensamines, a series of other medically useful monomeric naphthylisoquinoline alkaloids and derivatives thereof has been described (Francois et al., *Phytochemistry*, 35, 1461–1464, 1994; Francois et al., U.S. patent application Ser. No. 08/195,547). Similar to the korupensamines, these "non-korupensamine" monomeric naphthylisoquinoline alkaloids have been in exceedingly limited supply since they also are obtained from scarce plants having a limited geographic distribution. These other monomeric naphthylisoquinoline alkaloids differ from the korupensamines in their lack of a C-8' to C-5 naphthalene/isoquinoline linkage.

Accordingly, it is an object of the present invention to provide methods of chemically synthesizing known and new monomeric naphthylisoquinoline alkaloids, including korupensamines, derivatives thereof, and other monomeric naphthylisoquinolines (i.e., those lacking a C-8' to C-5 naphthalene/isoquinoline linkage).

Correspondingly, it is another object of the present invention to provide new monomeric naphthylisoquinoline compounds. Such compounds have particular use as therapeutic agents, for instance, as antiparasitic agents, and/or may serve as precursors or building blocks for the synthesis of dimeric naphthylisoquinoline compounds, such as exemplified by the michellamines (Bringmann et al., *Tetrahedron*, 50, 9643–9648, 1994; concurrently filed Bringmann et al., U.S. patent application; Boyd et al., *J. Med. Chem.*, 37, 1740–1745, 1994), which have proven to be medically useful.

These and other objects and advantages of the present invention, as well as additional inventive features, will be apparent from the description of the invention provided herein.

BRIEF SUMMARY OF THE INVENTION

The present invention provides a method of preparing a monomeric naphthylisoquinoline alkaloid comprising (a) preparing a naphthalene building block with at least one activation group at a coupling site and, optionally, with at least one protective group as a precursor to a free hydroxyl group desired in the monomeric naphthylisoquinoline alkaloid, (b) preparing an isoquinoline building block with at least one activation group at a coupling site and, optionally, with at least one protective group as a precursor to a free hydroxyl group desired in the monomeric naphthylisoquinoline alkaloid, wherein the isoquinoline building block is a tetrahydroisoquinoline, dihydroisoquinoline, or fully aromatic isoquinoline building block, and (c) coupling the naphthalene and isoquinoline building blocks at the coupling sites to form the monomeric naphthylisoquinoline alkaloid. The present invention also provides new monomeric naphthylisoquinoline alkaloids and derivatives thereof.

BRIEF DESCRIPTION OF THE DRAWINGS

FIG. 2 illustrates the preparation of the naphthalene building block 1-bromo-4-isopropoxy-5-methoxy-7-methylnaphthalene, which comprises the first stage of the method for preparation of korupensamines A and B. Reaction conditions: (a) NaH, THF, 24 h, 0° C. RT, 61%; (b) $CF_3CO_2H/H_2O$, 10 h, RT, 99%; (c) $Ac_2O$, 14 h reflux; (d) EtOH/EtONa, THF, 1 h, 95% from 3; (e) $Me_2SO_4$, acetone, $K_2CO_3$, reflux, 15 h, 99%; (f) $LiAlH_4$, THF, 1 h, 0° C., 95%; (g) $(BrCCl_2)_2$ (Bringmann and Schneider, *Synthesis*, 139–141, 1983), $CH_2Cl_2$, 30 min, RT, 95%; (h) L-selectride, $CH_2Cl_2$, 2.5 h, 0° C., 98%.

FIG. 3 illustrates the preparation of the isoquinoline building block 7, which comprises the second stage of the method for preparation of korupensamines A and B. Reaction conditions: (a) BnBr, 2N NaOH, $CH_2Cl_2$, $nBu_3NBnCl$, 5 h, RT; (b) iPrSNa, DMF, NaOH 150° C., 5 h, 56% from 6; (c) BnBr, 2 N NaOH, $CH_2Cl_2$, $nBu_3NBnCl$, 2 h, RT, 91%; (d) $Br_2$, DMF, 3 d, RT, 94%.

DETAILED DESCRIPTION OF THE INVENTION

Figure 1:
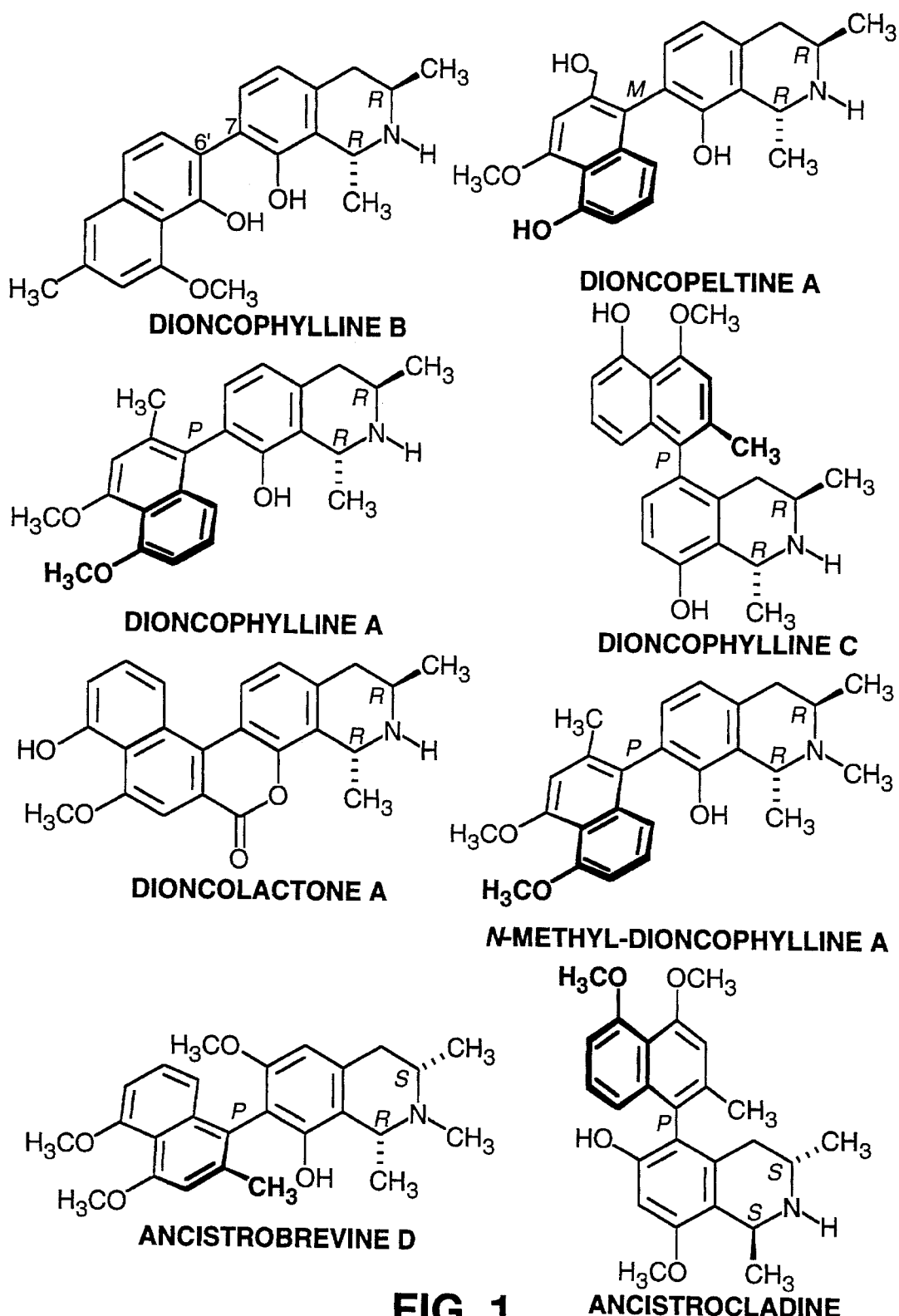
FIG. 1 illustrates the structures of non-korupensamines and other monomeric naphthylisoquinoline alkaloids lacking a C-8' to C-5 naphthalene/isoquinoline linkage.
Figure 1:
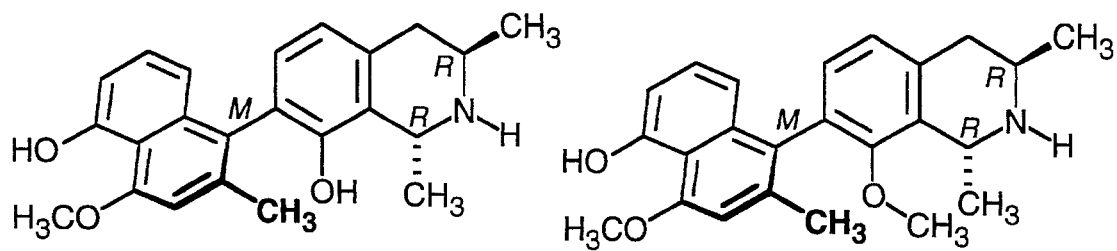
Figure 1:
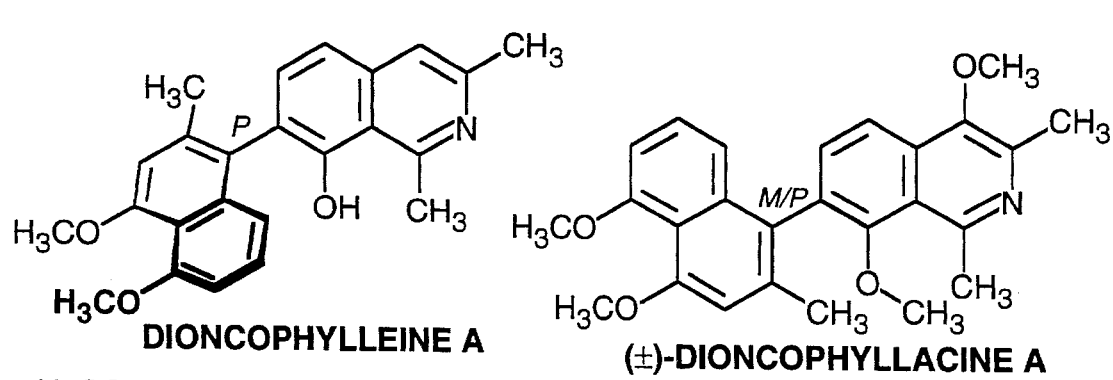
Figure 1:
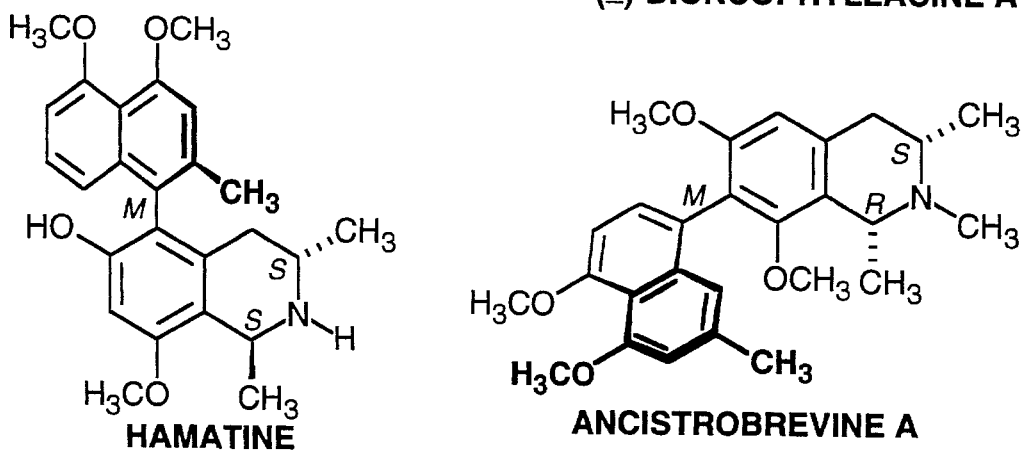
Figure 1:
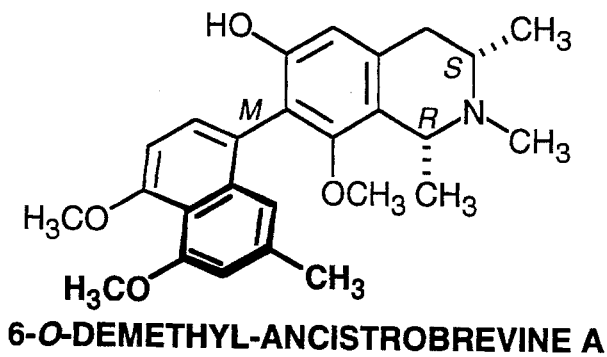
Figure 1:
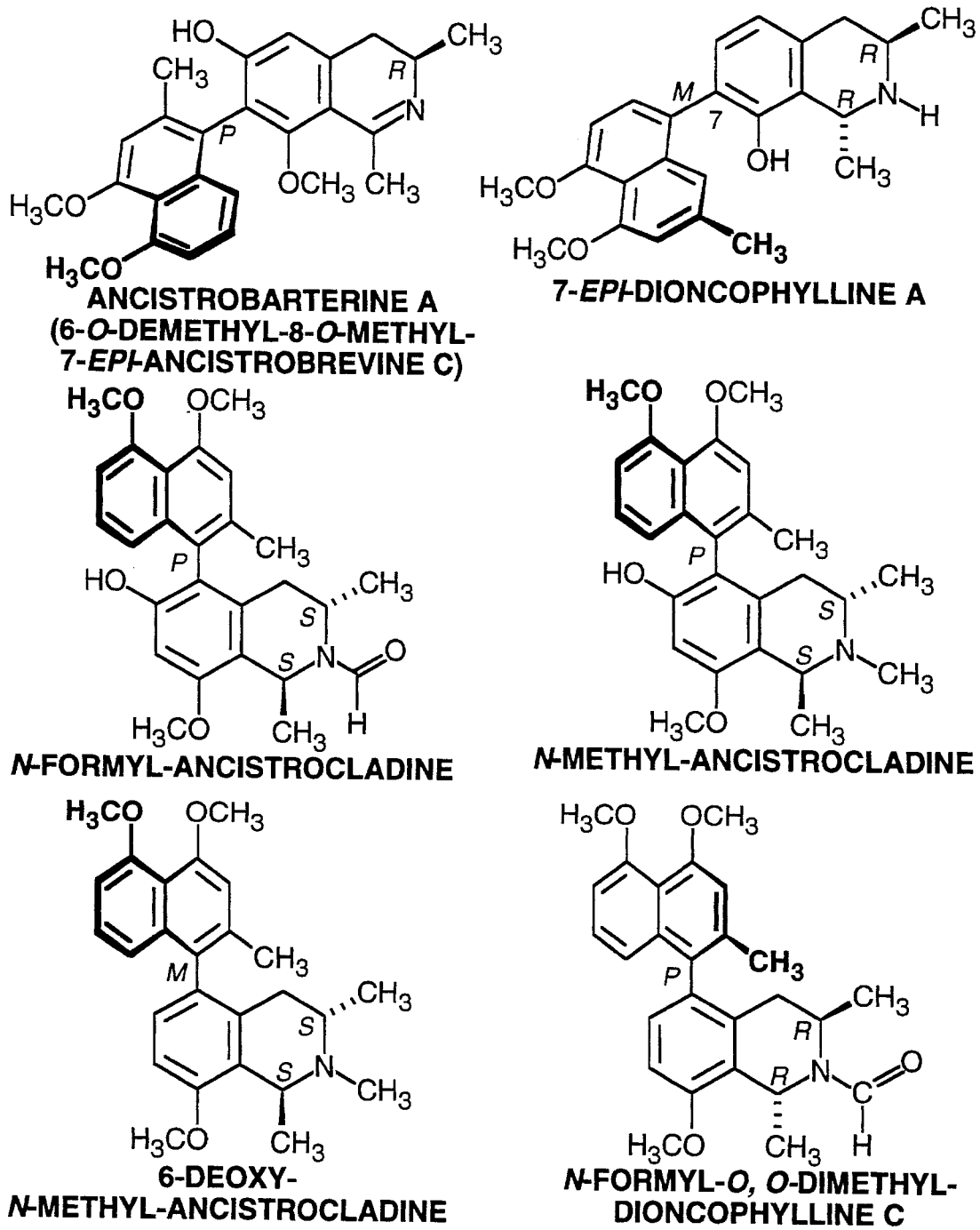
Figure 1:
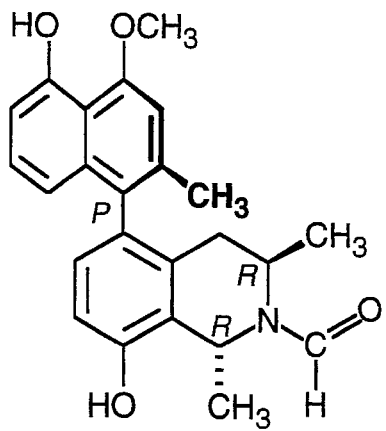
Figure 1:
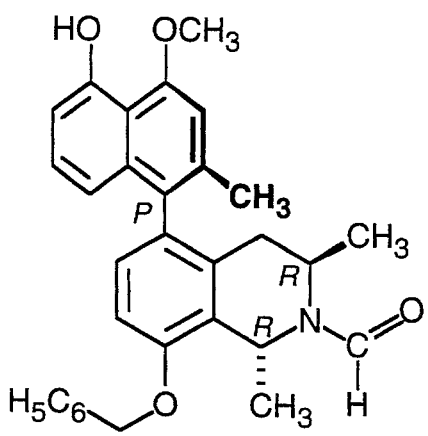
Figure 1:
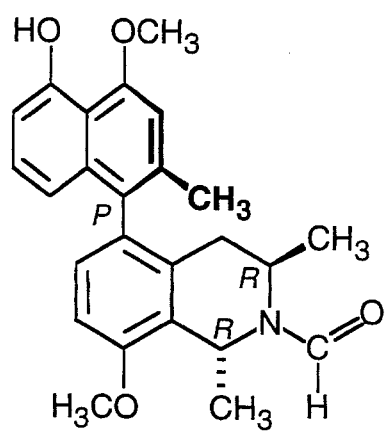
Figure 1:
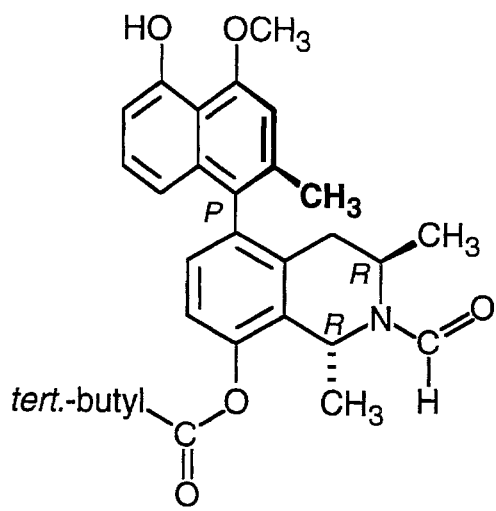
Figure 1:
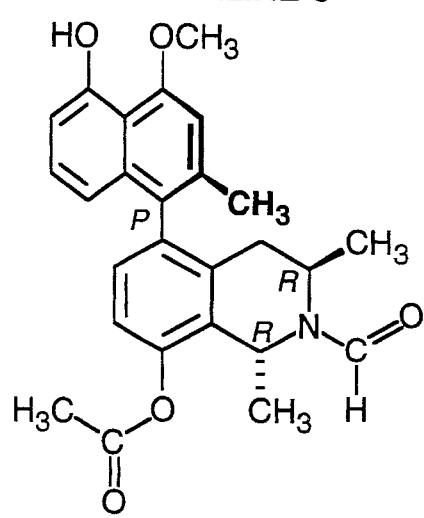
Figure 1:
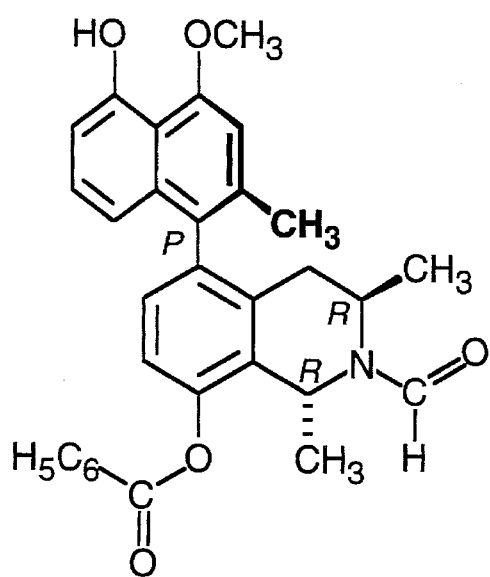
Figure 1:
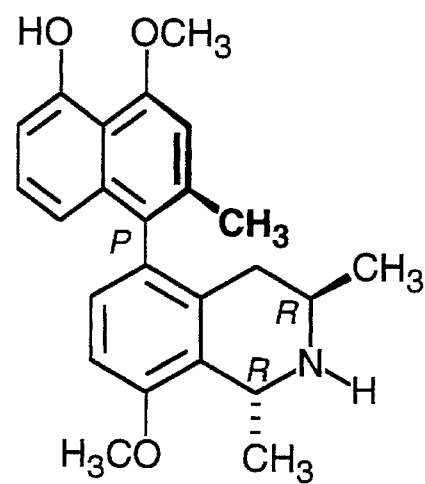

The present invention provides methods of preparing both known and new monomeric naphthylisoquinoline alkaloids and derivatives thereof. The present invention also provides new monomeric naphthylisoquinoline alkaloids and derivatives thereof.

Definitions

For clarification of the chemical structures described herein, the following definitions apply.

By "korupensamine" or "related monomeric naphthylisoquinoline alkaloids" is meant a monomeric naphthylisoquinoline alkaloid possessing a C-8' to C-5 naphthalene/isoquinoline linkage.

By "non-korupensamine" or "other monomeric naphthylisoquinoline alkaloids" is meant a monomeric naphthylisoquinoline alkaloid which lacks a C-8' to C-5 naphthalene/isoquinoline linkage.

By $C_1$–$C_6$ alkyl is meant straight or branched-chain $C_1$–$C_6$ alkyl groups. Examples include, but are not limited to, methyl, ethyl, n-propyl, isopropyl, n-butyl, isobutyl, sec-butyl, tertiary-butyl, n-pentyl, isopentyl, and n-hexyl.

By aryl is meant an organic radical derived from an aromatic hydrocarbon. Examples of aryl groups include phenyl and o-, m-, and p-hydroxyphenyl.

By aliphatic is meant an organic radical derived from an open hydrocarbon chain. Examples of aliphatic radicals include alkanes, alkenes, and alkynes. Specific examples of aliphatic radicals which can be used in the present invention include, but are not limited to, $C_1$–$C_6$ alkyl radicals, straight or branched.

Structures

To make it easier to compare naphthylisoquinoline alkaloids of the present invention of different coupling types, contrary to IUPAC numbering conventions, and consistent with previous work by the inventors (Bringmann et al., *Phytochemistry*, 30, 3845–3847, 1991), the naphthalene portion of the alkaloids is hereinafter numbered in the same way. In other words, there is always attributed a 2-methyl-4,5-dioxy-substitution pattern to the naphthalene, independent from the site of the axis.

Medical Uses

The new monomeric naphthylisoquinoline alkaloids and derivatives thereof are expected to have at least those medicinal properties possessed by the previously known monomeric naphthylisoquinoline alkaloids. The medically useful properties of the new compounds of the present invention can be confirmed or demonstrated using any of a variety of methods published or otherwise disclosed elsewhere. For example, in vitro and in vivo antimalarial activity may be confirmed as described in Francois et al., *Phytochemistry*, 35, 1461–1464, 1994, Francois et al., U.S. patent application Ser. No. 08/195,547, and Boyd et al., U.S. Pat. No. 5,409,938.

Synthesis of Monomeric Naphthylisoquinoline Alkaloids

The present inventive method of preparing a monomeric naphthylisoquinoline alkaloid comprises:

(a) preparing a naphthalene building block with at least one activation group at a coupling site and, optionally, with at least one protective group as a precursor to a free hydroxyl group desired in the monomeric naphthylisoquinoline alkaloid, (b) preparing an isoquinoline building block with at least one activation group at a coupling site and, optionally, with at least one protective group as a precursor to a free hydroxyl group desired in the monomeric naphthylisoquinoline alkaloid, wherein the isoquinoline building block is a tetrahydroisoquinoline, dihydroisoquinoline, or fully aromatic isoquinoline building block, and (c) coupling the naphthalene and isoquinoline building blocks at the coupling sites to form the monomeric naphthylisoquinoline alkaloid.

Preferably, the present inventive method further comprises:

(d) removing the protective groups from the monomeric naphthylisoquinoline alkaloid, and (e) purifying the monomeric naphthylisoquinoline alkaloid.

Any suitable building blocks can be utilized. The building blocks can have the configurations at any chiral centers as desired in the monomeric naphthylisoquinoline alkaloid. When the isoquinoline building block is a tetrahydroisoquinoline building block, the tetrahydroisoquinoline building block preferably has methyl groups at C-1 and C-3 and can have the R-configuration at C-1 and the R-configuration at C-3, the S-configuration at C-1 and the R-configuration at C-3, the R-configuration at C-1 and the S-configuration at C-3, or the S-configuration at C-1 and the S-configuration at C-3. Similarly, when the isoquinoline building block is a dihydroisoquinoline building block, the dihydroisoquinoline building block preferably has a methyl group at C-3 and can have either the S-configuration or the R-configuration at C-3.

Any suitable activation and protective groups can be utilized with respect to the building blocks. One of the activation groups, either on the naphthalene or isoquinoline building block, will generally be a nucleophilic activation group, while the other of the activation groups, on the other building block, will generally be an electrophilic activation group. The nucleophilic activation group is preferably selected from the group consisting boronic acid and trialkylstannyl groups. The electrophilic activation group is preferably selected from the group consisting of halogen and O-triflate leaving groups. The protective group is preferably an isopropyl group.

The aforementioned process steps can be carried out by any suitable means. Thus, for example, the coupling can be effected by several means, such as by transition metal catalysis, especially by using Pd. Also, the monomeric naphthylisoquinoline alkaloid can be purified by a variety of means, preferably by HPLC. The purification of the monomeric naphthylisoquinoline alkaloid is more preferably carried out by HPLC on an amino-bonded or other phase column so as to obtain a pure atropodiastereomer. Moreover, while the purification process is preferably carried out after removal of the protective groups, the purification process can be carried out either before or after the removal of the protective groups.

The distinct novelty of the aforementioned synthetic strategy includes both the intermolecular biaryl coupling of intact isoquinolines and naphthalenes (only Sargent in Australia did intermolecular coupling, but never managed to do that with the intact halves, cp. Rizzacasa and Sargent, *J.*

*Chem. Soc. Chem. Commun.*, 301, 1989) and also the use of the isopropyl and related protective groups as a precursor to the free OH-group on the naphthalene portion of the alkaloid. The latter is the basis for the synthesis of the naphthalene portion of monomeric alkaloids which possess the OH/OMe-pattern on the naphthalene portion of the alkaloid.

The preparation of a korupensamine or related monomeric naphthylisoquinoline alkaloid containing the C-8' to C-5 naphthalene/isoquinoline linkage comprises the aforedescribed general method wherein the coupling of the naphthalene and isoquinoline building blocks is by forming a C-8' to C-5 naphthalene/isoquinoline linkage, preferably wherein the activation group for the naphthalene building block is trialkylstannyl, the activation group for the isoquinoline building block is bromine, and the protective group is an isopropyl group. Similarly, the preparation of a non-korupensamine or other monomeric naphthylisoquinoline alkaloid which does not contain the C-8' to C-5 naphthalene/isoquinoline linkage comprises the aforedescribed general method wherein the coupling of the naphthalene and isoquinoline building blocks is by forming a naphthalene/isoquinoline linkage other than a C-8' to C-5 naphthalene/isoquinoline linkage, preferably wherein the activation group for the naphthalene building block is trialkylstannyl or a boronic acid group, the activation group for the isoquinoline building block is a halogen or an O-triflate leaving group, and the protective group is an isopropyl group.

Korupensamines, Related Monomeric Naphthylisoquinoline Alkaloids, and Derivatives Thereof The korupensamines and korupensamine derivatives of the present invention are chemically unique in several respects. Their basic structure comprises a biaryl system consisting of a tetrahydrogenated isoquinoline moiety with an unprecedented methyl group at C-3. Moreover, these alkaloids display atropisomerism due to the bulky ortho-substituents adjacent to the biaryl axis. Such highly unusual structures presumably result from an unprecedented biogenetic origin, for which a polyketide pathway has been implicated (Bringmann, *The Alkaloids*, Vol 29 (Brossi, ed.), Academic Press, New York, 1986, pp. 141–184; Bringmann et al., *Planta Med.*, 57, suppl. 2, 98, 1991). The korupensamines and korupensamine derivatives of the present invention are unique among all heretofore known naphthylisoquinoline alkaloids in containing only one C-8' to C-5 linkage of a naphthalene group and a tetrahydroisoquinoline group, an R configuration at C-1, and an exceptionally high polarity.

Korupensamines and derivatives are medically useful, for example, as antimalarial agents (Francois et al., U.S. patent application Ser. No. 08/195,547; Boyd et al., U.S. Pat. No. 5,409,938). Also, such "monomeric" compounds are chemically useful as precursors to medically useful (e.g. antiviral) "dimeric" compounds, such as michellamines (Boyd et al., *J. Med. Chem.*, 37, 1740–1745, 1994; Boyd et al., U.S. patent application Ser. No. 08/049,824; concurrently filed Bringmann et al., U.S. Patent Application). Previously, the only known source of korupensamines was a rare African plant (see, e.g., Hallock et al., 1994, supra; Boyd et al., 1994, supra).

The following synthetic procedure for korupensamine A and B provides a specific illustration of the preparation of monomeric naphthylisoquinoline alkaloids having a C-8' to C-5 naphthalene/isoquinoline linkage. Characteristic structural demands for the synthesis of the korupensamines are not only the high degree of free OH and NH functions (and thus the need for appropriate protective groups), but also the unusual position of the biaryl axis. In contrast to the various related alkaloids previously prepared by the "lactone methodology" (see, e.g., Bringmann et al., *Angew. Chem. Int. Ed. Engl.*, 25, 913–915, 1986; Bringmann and Reuscher, *Angew. Chem. Int. Ed. Engl.*, 25, 1672–1673, 1989; Bringmann and Jansen, *Synthesis*, 825–827, 1991), the monomeric naphthylisoquinolines, korupensamines A and B with the 8', 5-coupling type do not have a $C_1$ side-chain in an ortho-position next to the axis. Consequently the efficient "lactone methodology" is not applicable to this target biaryl. Accordingly, the present invention provides an intermolecular coupling strategy for the construction of the axis. As a precursor to the isocyclic moiety of the korupensamines, with the free hydroxy function specifically only at C-5' and the methylether at C-4' the naphthalene building block 4, with an O-isopropyl substituent as a protective group and the bromo substituent at the scheduled coupling position, is used. The method for construction of 4 is related to the preparation of related dimethoxy analogs except for the protective group strategy and is outlined in FIG. 2 and further described in Example 1.

FIG. 3 outlines the preparation of the next building block in the synthetic route to korupensamines A and B, the isoquinoline moiety. As a precursor for the heterocyclic moiety of the target molecules, the tetrahydroisoquinoline 7, i.e., with benzyl groups for the protection of both N-and O-functionalities, and again a bromine substituent at the site of the scheduled biaryl coupling, is used. For its preparation, the correctly 1R,3R-configurated tetrahydroisoquinoline 6, the directed synthesis of which from the aryl-propanone 5 has already been described (Bringmann et al., *Liebigs Ann. Chem.*, 877–888, 1993), is used. Whereas O-demethylation of 6 and subsequent double benzylation turns out to be very tedious, better results can be obtained by a stepwise O-benzylation/O-demethylation/O-benzylation sequence, followed by a regioselective bromination in the 5-position of the tetrahydroisoquinoline, to give 7. Additional details are included in Example 1.

Figure 4:
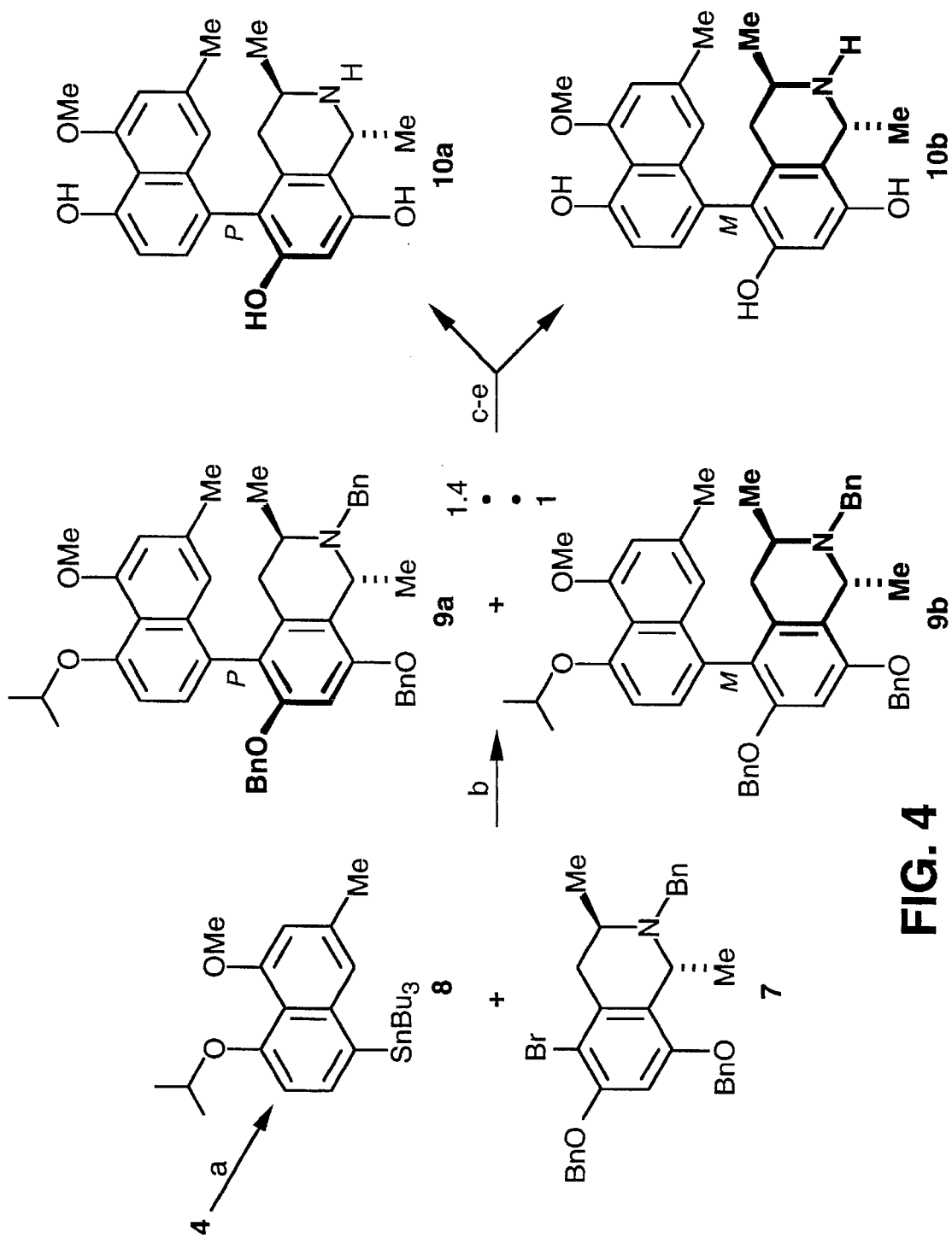
FIG. 4 illustrates the convergent construction of the monomeric naphthylisoquinoline alkaloids, which comprise the third and final stage of the method for preparation of korupensamines A and B. Reaction conditions: (a) tBuLi, $Bu_3SnCl$, THF, 2 h, −78° C., RT, 89%; (b) $PdCl_2(PPh_3)_2$, $PPh_3$, LiCl, Cu(I)Br, DMF, 40 h, 135° C., 15%; (c) $BCl_3$, $CH_2Cl_2$, 10 min, RT; (d) $H_2$, Pd/C, MeOH; (e) atropodiastereomer separation according to Hallock et al. (1994, supra).

FIG. 4 outlines the Pd(II) catalyzed intermolecular biaryl coupling of the suitably protected and activated building blocks. For the activation of the coupling sites, considering options such as halogen or O-triflate leaving groups on the electrophilic partner and boronic acid or trialkylstannyl groups on the nucleophilic partner, the use of a brominated isoquinoline 7 and a stannylated naphthalene 8 turns out to be the combination of choice in the case of korupensamines A and B. The tribenzyl derivative 7 can be coupled with 8 in good yields, giving a mixture of the two atropodiastereomers 9a and 9b, which without resolution may then be immediately deprotected by treatment with $BCl_3$ to cleave the isopropyl and benzyl ether functions, and subsequently treated by catalytic hydrogenation to set free the amino group, giving a mixture of 10a and 10b. Final atropodiastereomeric separation can be achieved by HPLC on an amino-bonded phase column, as previously published (Hallock et al., 1994, supra). Additional details of the synthesis are found in Example 1.

Figure 5:
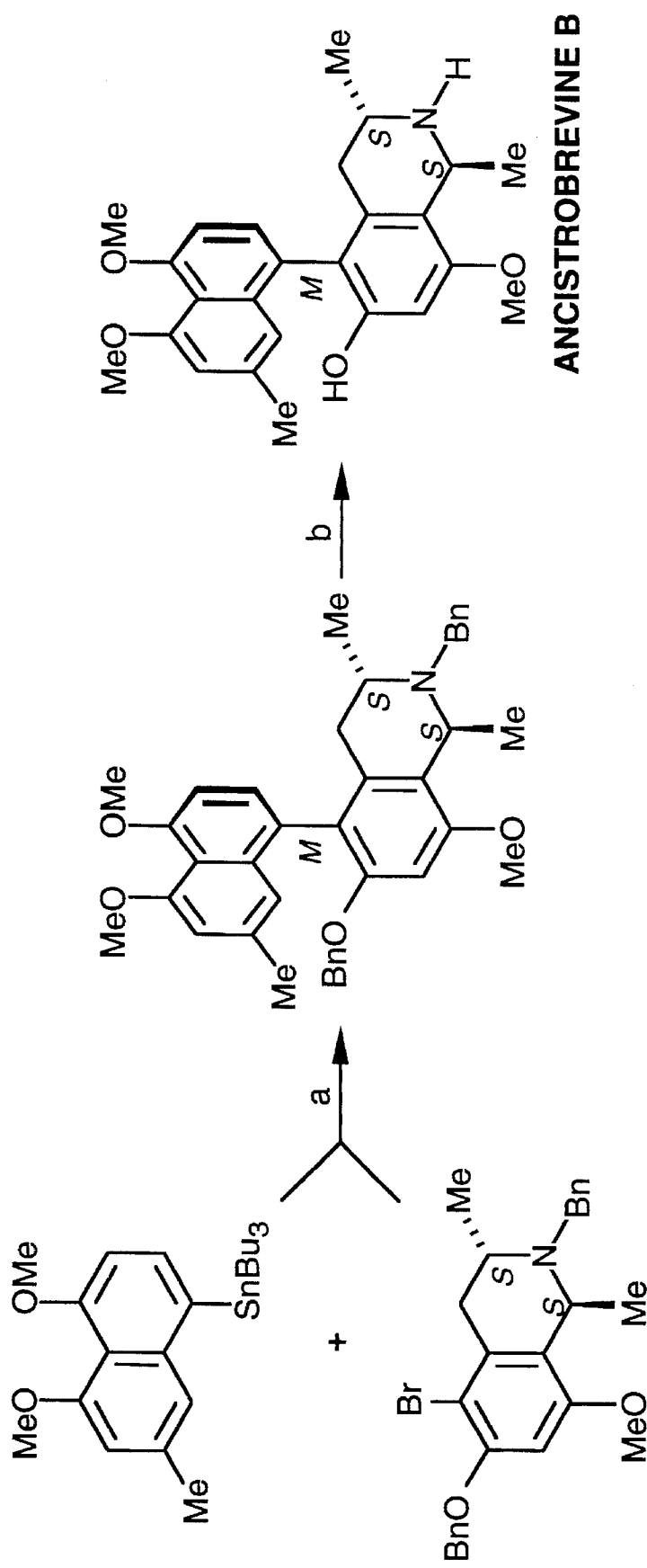
FIG. 5 illustrates the synthesis of ancistrobrevine B using the intermolecular coupling strategy of the present invention as described in Example 2. Reaction conditions: (a) $PdCl_2(PPh_3)_2$, LiCl, Cu(I)Br, DMF, 135° C.; (b) $H_2$, Pd/C, MeOH.

The present inventive method can be used to prepare monomeric naphthylisoquinoline alkaloids other than korupensamines. For example, FIG. 5 outlines a potential route of the synthesis of ancistrobrevine B using the intermolecular coupling strategy of the present invention.

One skilled in the art will readily appreciate that certain chemical modifications can be incorporated as desired into the precursors in the aforementioned synthetic method and/ or can be used to modify the end product thereof to obtain a useful new korupensamine or korupensamine derivative with modified biological properties. Such modified properties may include one or more of the following: greater therapeutic potency against a particular disease or disease-causing organism such as a parasite, particularly antimalarial potency, a broader spectrum of therapeutic activity against diverse diseases or disease-causing organisms such as a parasite, particularly against parasitic strains of malaria, enhanced oral bioavailability, less toxicity in a particular host mammal, more advantageous pharmacokinetics and/or tissue distribution in a given host mammal, and the like.

For example, a useful modified compound may be obtained by the methods of the present invention by selecting and constructing, and incorporating in the coupling step, an appropriately protected tetrahydroisoquinoline, dihydroisoquinoline, or fully aromatic isoquinoline building block having configurations at one or both of the chiral centers that are different from the corresponding naturally occurring korupensamines.

Moreover, by applying one or more chemical reactions (as disclosed in Francois et al., U.S. patent application Ser. No. 08/195,547 and Boyd et al., U.S. Pat. No. 5,409,938) to a given korupensamine or korupensamine derivative, a useful new derivative may be obtained wherein one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, a secondary amine site may instead be an amide, sulfonamide, tertiary amine, or alkyl quaternary ammonium salt or corresponding Hoffmann elimination product thereof, a tertiary amine site may instead be a secondary amine, and one or more aromatic hydrogen substituent(s) may instead be halo, nitro, amino, hydroxyl, thiol, or cyano.

Furthermore, by applying chemical reactions as disclosed herein to a given korupensamine or korupensamine derivative, a useful new derivative may be obtained wherein one or more aromatic hydrogen substituent(s) may instead be an acyl or $C_1$–$C_6$ alkyl substituent, and $CH_3$ may instead be H. These methods of derivatization are further described in Example 2.

Accordingly, the present invention provides a compound of the formula

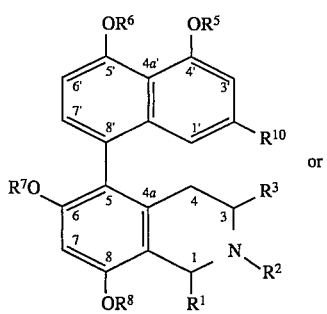

or

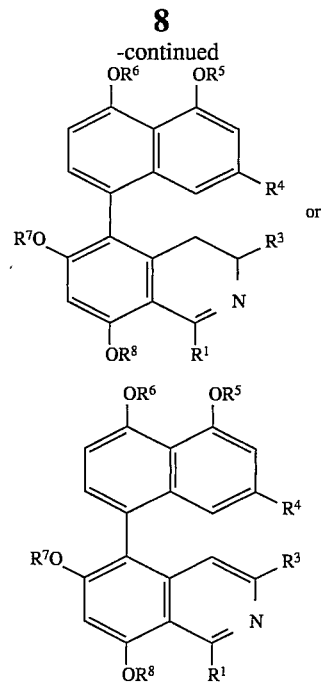

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl, or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, with the proviso that $R^{10}$ is not methyl when $R^1$ and $R^3$ are methyl.

The present invention also provides a compound of the same above-described structural formula wherein (a) $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl, or aryl, and one or more of the ring positions 1, 3, 4, 1', 2',3', 4', 5', 6', 7', 6, 7, and 8 may be substituted with halo, nitro, amino, hydroxyl, thiol, acyl, $C_1$–$C_6$ alkyl, or cyano, (b) one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, a tertiary amine site may instead be a secondary amine, and one or more aromatic hydrogen substituent(s) may instead be halo, nitro, amino, hydroxyl, thiol, or cyano, and (c) one or more aromatic hydrogen substituent(s) is instead an acyl or $C_1$–$C_6$ alkyl substituent. With respect to such a compound, $R^{10}$ may or may not be methyl when $R^1$ and $R^3$ are methyl.

Non-Korupensamines, Other Monomeric Naphthylisoquinoline Alkaloids, and Derivatives Thereof Numerous other naturally occurring, medically useful monomeric naphthylisoquinoline alkaloids and semisynthetic derivatives thereof have been identified (see, e.g., Francois et al., U.S. patent application Ser. No. 08/195,547 and references therein). These other alkaloids generally differ from korupensamines in their lack of a C-8' to C-5 naphthalene/isoquinoline linkage. As for the korupensamines, a practical, synthetic route of access to many of such compounds has not previously been available.

The above generally applicable method, having certain specific modifications or adaptations introduced on a case-by-case basis, may be used to prepare by chemical synthesis naturally occurring monomeric naphthylisoquinoline alkaloids lacking a C-8' to C-5 naphthalene/isoquinoline linkage, such as but not limited to the compounds identified in Table 1.

TABLE 1

Literature references reporting the chemical structures of naphthylisoquinoline alkaloids.

| Compound Name | Reference Citation |
|---|---|
| Dioncophylline B | Bringmann et al., Phytochemistry, 30, 3845–3847, 1991 |
| Dioncopeltine A | Bringmann et al., Phytochemistry, 30, 1691–1696, 1991 |
| Dioncophylline C | Bringmann et al., Phytochemistry, 31, 4019–4024, 1992 |
| Dioncolactone A | Bringmann et al., Phytochemistry, 30, 1691–1696, 1991 |
| Ancistrobrevine D | Bringmann et al., Planta Med., 58 (suppl 1), 703–704, 1992 |
| 5'-O-Demethyl-8-O-methyl-7-epi-dioncophylline A | Bringmann et al., Phytochemistry, 36 1057–1061 1994 |
| 5'-O-Demethyl-7-epi dioncophylline A | Bringmann et al., Planta Med., 59 (suppl), 621–622, 1993 |
| (±)-Dioncophyllacine A | Bringmann et al., Phytochemistry, 31, 4015–4018, 1992 |
| Ancistrobrevine A | Bringmann et al., Planta Med., 58 (suppl 1), 703–704, 1992 |
| 6-O-Demethyl-ancistrobrevine A | (unpublished) |
| Ancistrobarterine A (6-O-Demethyl-8-O-methyl-7-epi-ancistrobrevine C) | Bringmann et al., Planta Med., 59 (suppl), 623–624, 1993 |
| N-Formyl-O,O-dimethyl-dioncophylline C | Bringmann et al., Phytochemistry, 31, 4019–4024, 1992 |
| N-Formyl-dioncophylline C | Bringmann et al., Phytochemistry, 31, 4019–4024, 1992 |
| N-Formyl-8-O-benzyl-dioncophylline C | Francois et al., U.S. Pat. application Ser. No. 08/195,547 |
| N-Formyl-8-O-methyl-dioncophylline C | Francois et al., U.S. Pat. application Ser. No. 08/195,547 |
| N-Formyl-8-O-pivaloyl-dioncophylline C | Francois et al., U.S. Pat. application Ser. No. 08/195,547 |
| N-Formyl-8-O-acetyl-dioncophylline C | Francois et al., U.S. Pat. application Ser. No. 08/195,547 |
| N-Formyl-8-O-benzoyl-dioncophylline C | Francois et al., U.S. Pat. application Ser. No. 08/195,547 |
| 8-O-Methyl-dioncophylline C | Francois et al., U.S. Pat. application Ser. No. 08/195,547 |

The structures of these compounds identified in Table 1, for which no synthetic method of preparation has heretofore been published or otherwise disclosed, are shown in FIG. 1. Those compounds for which a synthetic method of preparation has heretofore been proposed, albeit quite different from the present inventive method, are identified in Table 2. The structures of these compounds are also depicted in FIG. 1.

TABLE 2

Literature references reporting the chemical structures of naphthylisoquinoline alkaloids.

| Compound Name | Reference Citation |
|---|---|
| Dioncophylline A | Bringmann et al., Tetrahedron Lett., 31, 639–642, 1990; Bringmann et al., Tetrahedron Lett., 31, 643–646, 1990 |
| N-Methyl-dioncophylline A | Bringmann et al., Phytochemistry, 30, 1307–1310, 1991 |
| Ancistrocladine | Bringmann, The Alkaloids, 29, 141–184, 1986 (and lit. cited therein) |
| N-Methyl-dioncophylline A (atropisomers) | Bringmann et al., Phytochemistry, 30, 1307–1310, 1991 |
| Dioncophylleine A | Fleischhauer et al., Z. Naturforsch, 48b, 140–148, 1993 |
| Hamatine | Bringmann et al., The Alkaloids, 29, 141–184, 1986; Bringmann et al., Angew Chem., 25, 913, 1986; Bringmann et al., Heterocycles, 28, 137, 1989 (and literature cited therein) |
| 7-epi-Dioncophylleine A | Bringmann et al., Tetrahedron Lett., 31, 643–646, 1990 |
| N-Formyl-ancistrocladine | Bringmann et al., Phytochemistry, 31, 4019–4024, 1992 |
| N-Methyl-ancistrocladine | Bringmann et al., Phytochemistry, 31, 4019–4024, 1992 (and literature cited therein) |
| 6-Deoxy-N-methyl-ancistrocladine | Bringmann et al., Phytochemistry, 31, 4019–4024, 1992 |

Thus, the present invention provides a method of preparing a compound having a formula selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O--demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O,O-dimethyldioncophylline C, N-formyl-dioncophylline C, N-formyl-8-benzyl-dioncophylline C, N-formyl-8-O-methyldioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and related alkaloids and derivatives thereof wherein the configurations at C-1 and C-3 may instead be the same or different and each may be R or S, the coupling points comprising the naphthalene/isoquinoline axis may be different, and the configuration about the axis may be different, i.e., M or P.

Figure 6:
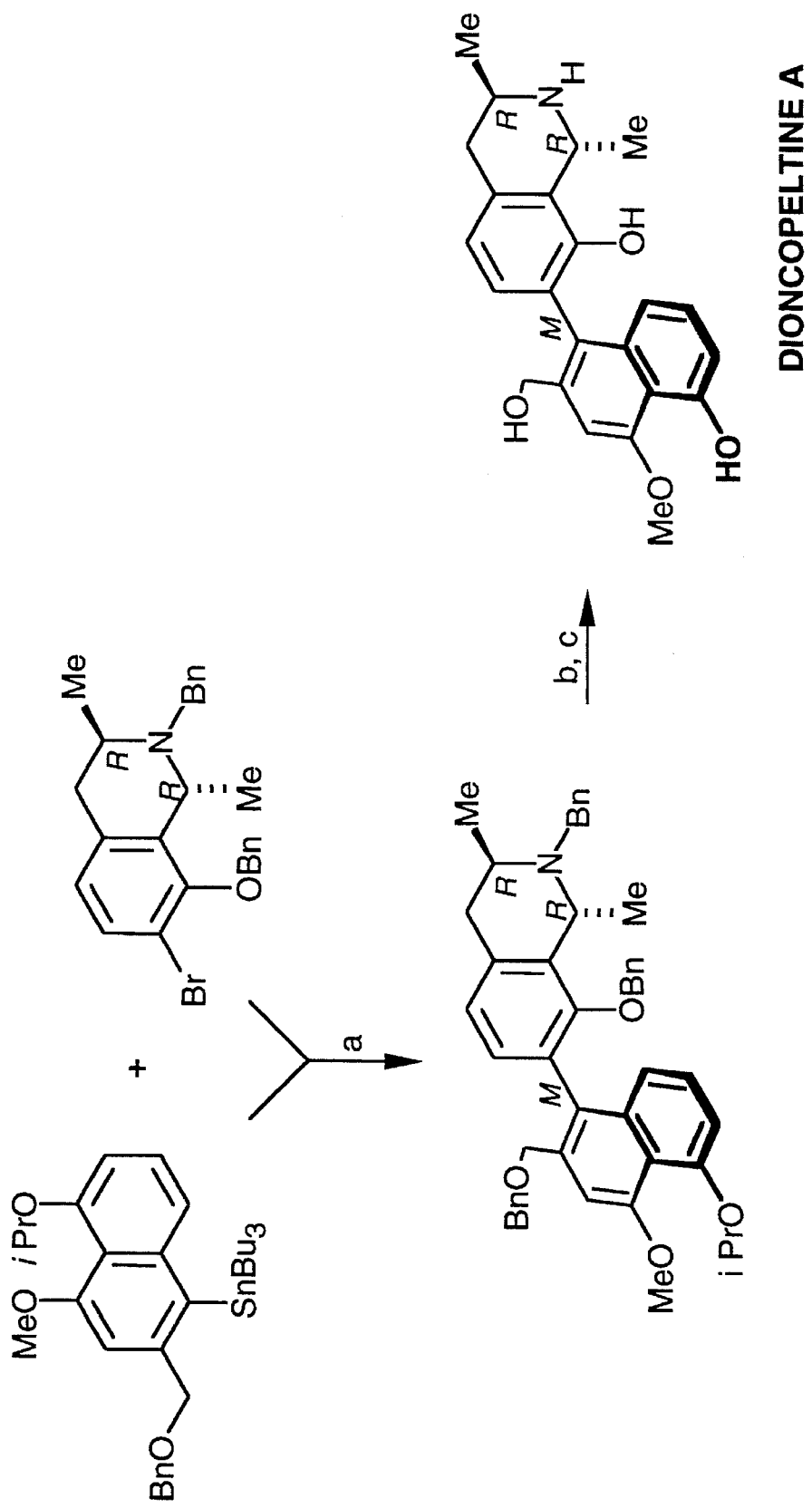
FIG. 6 illustrates the synthesis of dioncopeltine A using the intermolecular coupling strategy of the present invention. Reaction conditions: (a) $PdCl_2(PPh_3)_2$, LiCl, Cu(I)Br, DMF, 135° C.; (b) $BCl_3$ c) $H_2$, Pd/C, MeOH.
Figure 7:
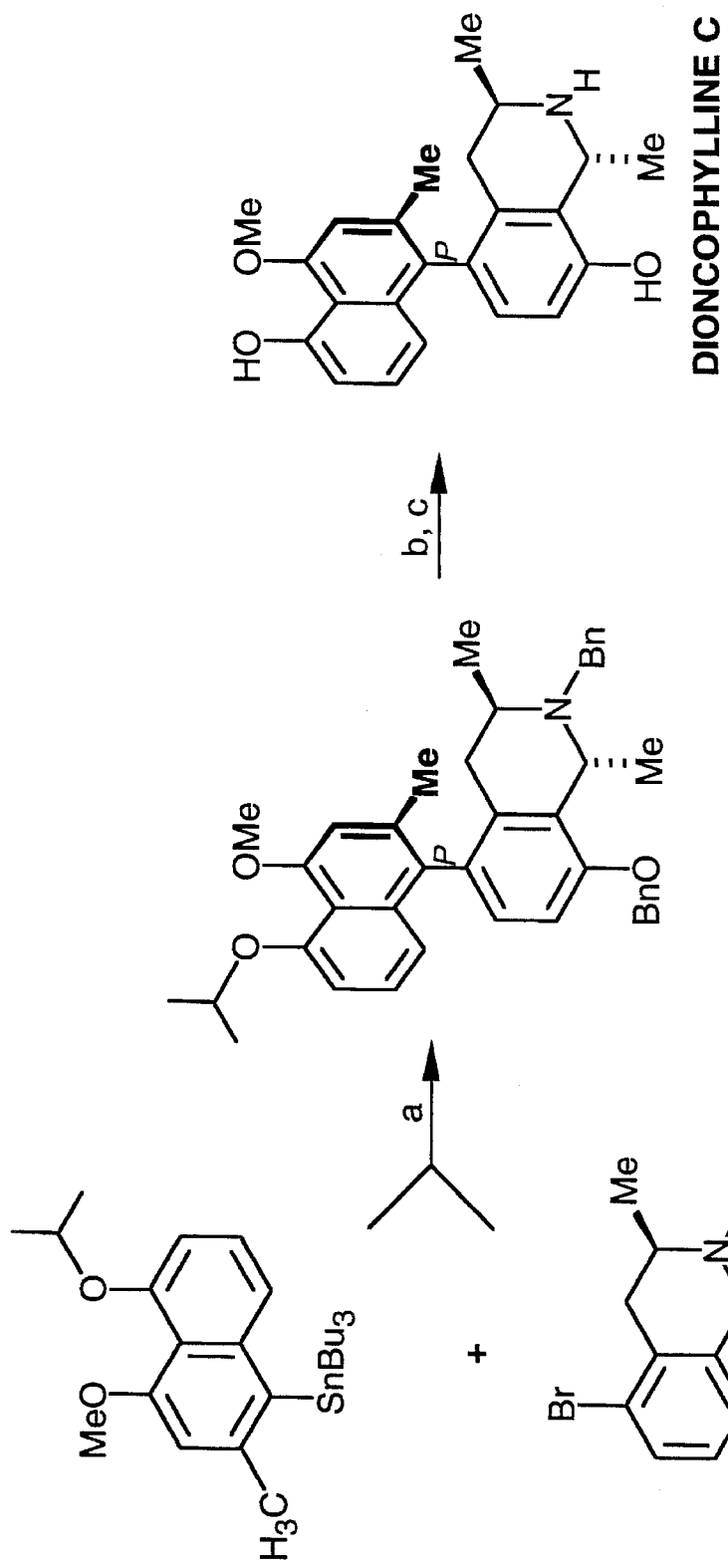
FIG. 7 illustrates the synthesis of dioncophylline C using the intermolecular coupling strategy of the present invention. Reaction conditions: (a) $PdCl_2(PPh_3)_2$, LiCl, Cu(I)Br, DMF, 135° C.; (b) $BCl_3$; (c) $H_2$, Pd/C, MeOH.

As more specific examples of the synthetic method of preparation, FIGS. 6 and 7 illustrate potential routes of the synthesis of dioncopeltine A and dioncophylline C, respectively, using the intermolecular coupling strategy of the present invention. Similar to the korupensamine synthesis, the desired appropriately protected and activated naphthalene and isoquinoline building blocks are subjected to the conditions giving the desired intermolecular biaryl coupling, then followed by deprotection and separation, or separation then deprotection, to give the desired product.

Moreover, by applying one or more chemical reactions (as disclosed in Francois et al., U.S. patent application Ser. No. 08/195,547 and Boyd et al., U.S. Pat. No. 5,409,938) to a given non-korupensamine or non-korupensamine derivative, a useful new derivative may be obtained wherein one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, a secondary amine site may instead be an amide, sulfonamide, tertiary amine, or alkyl quaternary ammonium salt or corresponding Hoffmann elimination product thereof, a tertiary amine site may instead be a secondary amine, and one or more aromatic hydrogen substituent(s) may instead be halo, nitro, amino, hydroxyl, thiol, or cyano. By way of the present invention, new compounds may be obtained, wherein, with respect to the aforementioned compounds, one or more aromatic hydrogen substituent(s) is instead an acyl or $C_1$–$C_6$ alkyl substituent, at least one $CH_3$ is instead H, and/or the tetrahydroisoquinoline is instead a dihydroisoquinoline or a fully aromatic isoquinoline. These methods of derivatization are described in Example 2.

Accordingly, the present invention provides a compound having a formula selected from the group consisting of dioncophylline B, dioncopeltine A, dioncophylline A, dioncophylline C, dioncolactone A, N-methyl-dioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O,O-dimethyldioncophylline C, N-formyl-dioncophylline C, N-formyl-8-O-benzyl-dioncophylline C, N-formyl-8-O-methyldioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein (a) the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, and one or more aromatic hydrogen substituent(s) may instead be halo, nitro, amino, hydroxyl, thiol, or cyano, and (b) one or more aromatic hydrogen substituent(s) is instead an acyl or $C_1$–$C_6$ alkyl substituent, at least one $CH_3$ is instead H, and/or the tetrahydroisoquinoline is instead a dihydroisoquinoline or a fully aromatic isoquinoline.

EXAMPLES

The following examples further illustrate the present invention, but, of course, should not be construed as in any way limiting its scope.

EXAMPLE 1

Synthesis of Monomeric Alkaloids

This example provides a description of the method of preparing monomeric alkaloids. In particular, this example provides a specific description of the preparation of korupensamine A (FIG. 4; 1ea) and korupensamine B (FIG. 4; 10b), both of which contain the characteristic C-8' to C-5 naphthalene/tetrahydroisoquinoline linkage. The reaction for other monomeric alkaloids is quite similar.

The first stage of the method corresponding to preparation of the naphthalene building block is illustrated in FIG. 2; the reaction conditions and yields are summarized in the corresponding legend. The synthesis starts with 1 (pale yellow oil), prepared by O-isopropylation (Pr-Br, acetone, 88%) and subsequent bromination ($Br_2$.NaOAc, $CH_2Cl_2$, 62%) of 3-hydroxybenzaldehyde. For the annulation of the second ring, the introduction of the missing $C_4$-unit by Wittig reaction proved to give higher yields than the Stobbe approach frequently used in the literature (Handford and Whalley, *J. Chem. Soc.*, 3896–3897, 1963). From the known building block 2 (Owton et al., *Syn. Commun.*, 23, 2119–2125, 1993, and literature cited therein) was obtained, after selective cleavage of the tert-butylester group with $CF_3CO_2H$, the α,β-unsaturated monoester 3 (m.p. 86° C.), which then was cyclized, O-deacetylated, and O-methylated. Transformation of the ester functionality into the required methyl substituent was brought about by LAH-reduction and subsequent deoxygenation of the primary alcohol group by hydroxy/halogen exchange (Bringmann et al., *Angew. Chem. Int. Ed. Eng.*, 913–915, 1986; Bringmann and Schneider, *Synthesis*, 139–141, 1983) followed by further reduction to give 4 (m.p. 78° C.).

2-Bromo-S-isopropoxy-benzaldehyde (1). To a suspension of 50.0 g (110 mmol) 3-hydroxybenzaldehyde and 100 g (725 mmol) dry $K_2CO_3$ in 100 mL dry DMF, 61.5 g (500 mmol) isopropylbromide was added at room temperature. The reaction mixture was heated for 17 h at 90° C. The solvent was removed under reduced pressure and the residue was partitioned between 2N NaOH and toluene. The collected organic layers were dried ($MgSO_4$), filtered and the solvent removed under pressure. The residue was distilled in vacuo to give 58.8 g (88%) colorless liquid. To a solution of 57.0 g (347 mmol) 3-isopropoxybenzaldehyde in 200 mL dichloromethane 30.5 g (372 mmol) NaOAc was added. After that a solution of 55.5 g (347 mmol) bromine in 50 mL dichloromethane was added dropwise and the reaction mixture was stirred overnight. The reaction mixture was extracted with saturated aqueous $Na_2SO_3$ and the combined organic phases were dried ($MgSO_4$), filtered and concentrated under reduced pressure. The residue was distilled in vacuo to give 1 (52.1 g, 62%) as a yellow oil.

2-tert-Butoxycarbonyl-1-ethoxycarbonylethyl idendiethoxyphosphorane (2). To a suspension of 5.50 g (231 mmol) NaH in 300 mL dry THF, a solution of 49.3 g (220 mmol) triethylphosphonoacetate in 150 mL dry THF under Ar at 0° C. was added dropwise. The reaction mixture was stirred and allowed to warm to room temperature overnight. 45.0 g (231 mmol) tert-butyl-bromoacetate was added dropwise at 0° C. over 30 min and the reaction mixture was allowed to warm to room temperature. After 28 h the reaction mixture was concentrated under reduced pressure and partitioned between water and ethyl acetate. The organic phase was dried ($MgSO_4$), filtered and concentrated under reduced pressure. The crude product was distilled in vacuo to give 54.0 g (73%) 2 as a viscous oil.

(E) -3-Carboethoxy-4-(2'-bromo-5'-isopropylphenyl)-3-butanic Acid (3). To a suspension of 1.85 g (77.1 mmol) NaH in 130 mL dry THF, 25.4 g (75.1 mmol) tert-butoxycarbonyl-1-ethoxycarbonylethylidendiethoxy-phosphorane (2) was added dropwise at 0° C., The reaction mixture was stirred for 6 h at 0° C. under Ar. This solution was added under Ar dropwise at 0° C. to 15.5 g (63.5 mmol) 2-bromo- 5-isopropoxy-benzaldehyde (1), dissolved in 80 mL dry THF. The cooling bath was removed and the reaction mixture was stirred overnight at room temperature. 20 mL water was added and the solvent was removed under reduced pressure. The residue was partitioned between water and dichloromethane. The organic layers were dried (MgSO$_4$), filtered and the solvent was removed under reduced pressure to afford 16.5 g (61%) (E)-3-carboethoxy-4-(2'-bromo-5-isopropylphenyl) -3-butenic acid-tert-butyl ester as a yellow oil.

15.0 g (35.1 mmol) of the crude (E)-3-carboethoxy-4-(2'-5-isopropylphenyl)-3-butenic acid-tert-butyl ester was dissolved in 70 mL 90% aqueous trifluoroacetic acid and stirred for 3 h. Removal of trifluoroacetic acid in vacuo afforded 12.8 g (99%) 3 as a pale yellow solid (m.p. 86° C.).

1-Bromo-4-isopropoxy-5-methoxy-7-methylnaphthalene (4). 12.9 g (34.8 mmol) (E)-3-carboethoxy-4-(2'-bromo-5'-isopropylphenyl)-3-butenic acid (3) were dissolved in 340 acetic anhydride and heated for 6 h in reflux. After cooling to room temperature, a solution of 200 g ice, 200 g water and 90 g K$_2$CO$_3$ were added. After extraction with dichloromethane, the combined organic layers were dried (MgSO$_4$), filtered and concentrated under reduced pressure. The dried residue was dissolved in a solution of 8.40 g (389 mmol) sodium in 300 mL dry ethanol and stirred for 4 h at room temperature under Ar. The solvent was removed in vacuo and the residue was partitioned between 100 mL dichloromethane and 30 mL 2N HCl-solution. The organic phases were collected, dried (MgSO$_4$) and concentrated under reduced pressure. The residue was recrystallized from isopropanol to give 11.7 g (95%) ethyl-8-bromo-4-hydroxy-5-isopropoxy-2-naphthoate as yellow crystals (m.p. 106° C.).

To a solution of 4.92 g (13.9 mmol) ethyl-8-bromo-4-hydroxy-5-isopropoxy-2-naphthoate in 150 mL acetone 4.80 g (34.8 mmol) K$_2$CO$_3$ and dropwise 4.90 g (38.7 mmol) dimethylsulfate at room temperature were added. Subsequently the reaction mixture was refluxed for 10 h and after that 60 mL of concentrated ammonia was added. Solvent was removed under vacuum and the residue was partitioned between water and dichloromethane. The combined organic phases were washed three times with 2N NaOH solution and two times with water. The organic phase was dried (MgSO$_4$) and concentrated under vacuum. The residue was recrystallized from diethylether to give 5.00 g (99%) ethyl-8-bromo-5-isopropoxy-4-methoxy-2-naphthoate as colorless needles (m.p. 62° C.).

A solution of 4.80 g (13.1 mmol) ethyl-8-bromo-5-isopropoxy-4-methoxy-2-naphthoate in 100 mL dry THF was cooled to 0° C. under Ar. A suspension of 498 mg (13.1 mmol) LiAlH$_4$ in 60 mL dry THF was cooled to 0° C. and added to the ester over a period of 45 min. After stirring for 30 min at 0° C., 10 mL water and 10 mL 2N HCl were added carefully. The THF was concentrated in vacuo and the residue was extracted with dichloromethane, dried (MgSO$_4$) and concentrated in vacuo. Column chromatography (dichloromethane/acetone, 95:5) afforded 4.00 g (95%) 1-bromo-7-hydroxymethyl-4-isopropoxy-5-methoxy-naphthalene as colorless needles (m.p. 120°–121° C.).

To a solution of 4.00 g (12.3 mmol) 1-bromo-7-hydroxymethyl-4-isopropoxy-5-methoxy-naphthalene in 40 mL dry dichloromethane, 3.24 g (12.3 mmol) triphenylphosphane and 4.00 g (12.3 mmol) 1,2-dibromotetrachloroethane were added under Ar. After stirring for 30 min at room temperature, the solvent was removed and subsequently the residue was filtered over a short silica gel column (petroleum/ethyl acetate, 4:1) to give 5.00 g (95%) 1-bromo-7-bromomethyl-4-isopropoxy-5-methoxy-naphthalene as a colorless solid (m.p. 126° C.).

To a 0° C. cold solution of 7.60 g (19.6 mmol) 1-bromo-7-bromomethyl-4-isopropoxy-5-methoxy-naphthalene in 150 mL dry dichloromethane, 20.0 mL (20.0 mmol) of a 1M L-selectride-solution was added under Ar. After 2 h, further 2.50 mL (2.50 mmol) 1M L-selectride-solution was added. After that the solvent was removed in vacuo and the residue was filtered over a short silica gel column (petroleum/acetone, 30:1). After removal of the solvent in vacuo, the residue was recrystallized from acetone to give 5.90 g (98%) of 4 as colorless needles (m.p. 78° C.).

The second stage of the synthesis corresponding to preparation of the isoquinoline building block is shown in FIG. 3. The reaction conditions and yields are summarized in the corresponding legend. 7: A solution of the isoquinoline 6 (1.50 g, 5.07 mmol), benzyl bromide (0.66 mL, 5.55 mmol) and benzyl tri-n-butyl ammonium chloride (160 mg, 0.51 mmol) in dichloromethane (20 mL) and 2N NaOH (8 mL) was stirred vigorously for 5 h at 20° C. The layers were separated, the aqueous layer was extracted with dichloromethane and dried over sodium sulfate. Chromatography on deactivated (5% NH$_3$) silica gel with petroleum ether/tert-butyl methyl ether/ethyl acetate (100:0:0→90:6:3) as eluent afforded the crude benzylated isoquinoline (1.58 g) as a yellow oil. (characterized as HBr salt; m.p. 232°–234° C., $[\alpha]_D^{20}$=+23 φ° (c=1.1 in ethanol)). To a suspension of sodium hydride (480 mg, 20.0 mmol) in dimethyl formamide (20 mL) 1-methyl ethanethiol (1.86 mL, 20.0 mmol) was added. The mixture was stirred for 0.5 h at 40° C. and then added to the crude benzylated isoquinoline. The resulting solution was heated to 150° C. for 5 h. At 20° C., water (50 mL) and saturated ammonium chloride solution (20 mL) were added. After stirring for 10 min, the phases were separated, and the aqueous layer was extracted with dichloromethane. Chromatography on deactivated (5% NH$_3$) silica gel with petroleum ether/tert-butyl methyl ether/ethyl acetate (100:0:0→70:20:10) as eluent yielded the starting material 6 (539 mg, 1.81 mmol) and the 6-hydroxy isoquinoline (688 mg, 1.84 mmol, 36%, 56% based on recovered starting material, characterized as HBr salt; m.p. 239° C., $[\alpha]_D^{20}$=+24° (c=0.53 in ethanol)). A solution of the 6-hydroxyisoquinoline (137 mg, 0.37 mmol), benzyl bromide (48 μL, 0.40 mmol) and benzyl tri-n-butyl ammonium chloride (11 mg, 37 μmol) in dichloromethane (6 mL) and 2N NaOH (3 mL) was stirred vigorously for 2 h at 20° C. The aqueous layer was extracted with dichloromethane. Chromatography on deactivated (5% NH$_3$) silica gel with petroleum ether/tert-butyl methyl ether/ethyl acetate (100:0:0→85:10:5) as eluent afforded the tribenzylisoquinoline (155 mg, 0.334 mmol, 91%) as a pale yellow oil. A solution of this oil (36 mg, 78 μmol) and bromine 7 μL, 130 μmol) in dimethyl formamide (1 mL) was stirred for 3 d at 20° C. The solution was diluted with dichloromethane, and bisulfite solution was added. Extraction with dichloromethane and chromatography on deactivated (5% NH$_3$) silica gel with petroleum ether/tert-butyl methyl ether/ethyl acetate (100:0:0→85:10:5) as eluent yielded the isoquinoline 7 (42 mg, 73 μmol, 94%) as a yellow oil. The resulting product 7 (characterized as its HCl salt: mp 130° C. $[\alpha]_D^{20}$=+36°, c=0.49 in acetone), provided the necessary precursor for the heterocyclic part of the target molecules.

The third stage of the synthesis corresponding to convergent construction of the alkaloids is shown in FIG. 4. The reaction conditions and yields are summarized in the corresponding legend. The coupling of the dibenzyl derivative 7 with 8 gave a mixture of the two atropodiastereomers 9a and 9b in a 1.4:1 ratio. Since both diastereomeric target molecules 10a and 10b occur in nature, and also since both were desired for subsequent synthesis of michellamines (e.g., see Example 3), the precursors 9a and 9b were not necessarily resolved, but were immediately deprotected by treatment with $BCl_3$ to cleave the isopropyl and benzyl ether functions. Subsequent catalytic hydrogenation gave the free amino forms of 10a and 10b, which were then isolated and purified individually by HPLC on an amino-bonded phase column as published (Hallock et al., supra). All compounds in all three of the above synthetic stages were verified to have the appropriate physicochemical, spectral and other analytical data.

The method of synthesis for other monomeric alkaloids (i.e., in particular, non-korupensamine alkaloids) is done using the same or similar chemical principles as is illustrated for korupensamine A and B. More detail regarding this technology is set forth in FIGS. 5–7.

EXAMPLE 2

Synthesis of Monomeric Alkaloid Derivatives

This example further illustrates methods for the preparation of medically useful new derivatives of naphthylisoquinoline alkaloids which are either naturally occurring or are prepared according to the aforementioned methods of the present invention and which either may be a korupensamine, a related monomeric naphthylisoquinoline alkaloid, a non-korupensamine, or other monomeric naphthylisoquinoline alkaloid.

Using standard organic chemical methodology (particularly as set forth in Francois et al., U.S. patent application Ser. No. 08/195,547 and Boyd et al., U.S. Pat. No. 5,409,938, as well as set forth herein), one or more structural modifications of the aforementioned synthetic naphthylisoquinoline alkaloids can be made to provide derivatives with modified biological properties which may advantageously be useful for treatment of certain host mammal species and/or against certain pathogenic agents, particularly parasitic species such as strains of malaria. Such properties may, for example, include one or more of the following: greater therapeutic potency, particularly antimalarial potency; broader spectrum of therapeutic activity, particularly antimalarial activity; enhanced oral bioavailability; less host toxicity; and more advantageous pharmacokinetics and/or tissue distribution.

Depending on the stoichiometric amount of the particular reactant, the naphthylisoquinoline compound can be substituted at one, some, or all of the respective available positions. For example, when such a compound is reacted with a certain amount of $CH_3COCl$, acetate can be introduced at one, some, or all the available OH or NH positions.

Examples of these include, but are not limited to:

1. Conversion to ester, sulfonate ester, and ether substituents at one or more phenolic hydroxyl positions in the naphthylisoquinoline compound.

For example, for preparation of esters or sulfonate esters, the selected naphthylisoquinoline compound can be reacted with an acid halide (RCOX or $RSO_2X$, where X=Cl, Br, or I, and R is an $C_1$–$C_6$ aliphatic or aromatic radical) in anhydrous pyridine or triethylamine.

Alternatively, the selected compound may be reacted with an acid ($RCO_2H$ or $RSO_3H$ wherein R is an aliphatic or aromatic radical) and dicyclohexylcarbodiimide in triethylamine to prepare the ester or sulfonate ester.

For preparation of ethers, the selected naphthylisoquinoline compound is reacted with an organic halide (e.g., RX, $RCH_2$—X (where X=Cl, Br, or I), OTf, or OTs, and R is a $C_1$–$C_6$ aliphatic or aromatic radical) in anhydrous acetone with anhydrous potassium carbonate or with phase transfer catalysis.

For instance:

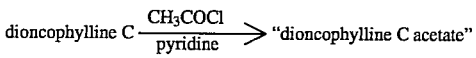

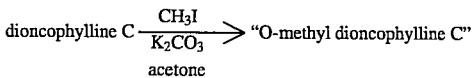

2. Removal of (an) ether methyl group(s) to provide a phenolic hydroxyl functionality and/or conversion of that moiety to an ester, sulfonate, or other ether.

For example, for hydrolytic cleavage of the methyl ether and conversion to phenolic hydroxyl, the selected naphthylisoquinoline compound is reacted with $BBr_3$, $BX_3$·$(CH_3)_2S$ in $CH_2Cl_2$ (where X=F, Cl or Br), FtS, or other ether cleaving reactants. The resulting phenol can be converted to esters, sulfonate esters or ethers as described above.

For instance:

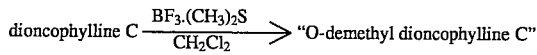

3. Preparation of amide or sulfonamide derivatives at the amine site in a selected naphthylisoquinoline compound.

For example, for preparation of amide or sulfonamide derivatives, the same general procedures described above (in 1) apply. In either case (1 or 3), an appropriate functional group protection strategy (blocking/deblocking of selected groups) is applied.

For instance:

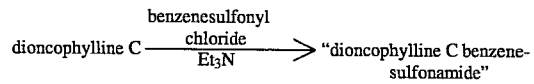

4. Conversion of the secondary amine functionality to an alkyl quaternary ammonium salt or to a tertiary amine.

For example, for preparation of tertiary amines, the selected naphthylisoquinoline alkaloid is reacted with an aldehyde and the resulting product reduced with $NaBH_4$.

Alternatively, for preparation of an alkyl ammonium salt, the selected naphthylisoquinoline alkaloid is reacted with an alkyl halide (RX, where X=Cl, Br or I, and R is an $C_1$–$C_6$ aliphatic radical) in anhydrous aprotic solvent.

For instance:

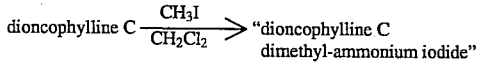

5. Conversion of the tertiary amine function to a secondary amine.

For example, for preparation of a secondary amine, a selected N-alkyl naphthylisoquinoline compound is reacted with cyanogen bromide to give the corresponding cyanamide, which is then treated with $LiAlH_4$.

For instance:

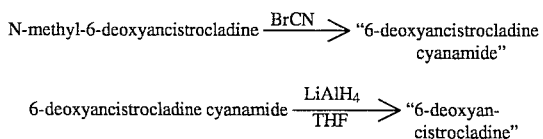

6. Conversion of one or more phenolic hydroxyl groups to an aromatic hydrogen substituent.

For example, the selected naphthylisoquinoline compound is converted (after suitable protection of the amine function if necessary) to the triflic ester, followed by reductive deoxygenation of the triflic ester to give the corresponding derivative.

For instance:

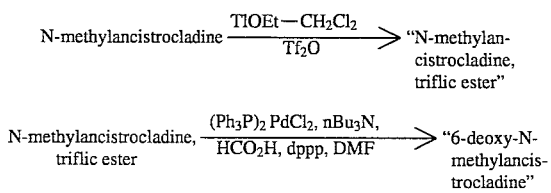

7. Substitution of one or more hydrogen substituents on the aryl systems by halogen, nitro, amino, hydroxyl, thiol, or cyano groups.

For example, for preparation of bromine-substituted derivatives, the selected naphthylisoquinoline compound is reacted with $Br_2$ in $H_2O$. For preparation of other substituted derivatives, the selected naphthylisoquinoline compound is treated with $HNO_3/HOAc$ to provide nitro-substituted ($-NO_2$) derivatives. In turn, the nitro derivative can be reduced to the amino derivative. The amino-derivative is the point of origin of the chloro, iodo, cyano, thiol, and hydroxyl substitution via well known and practiced diazonium substitution reactions.

For instance:

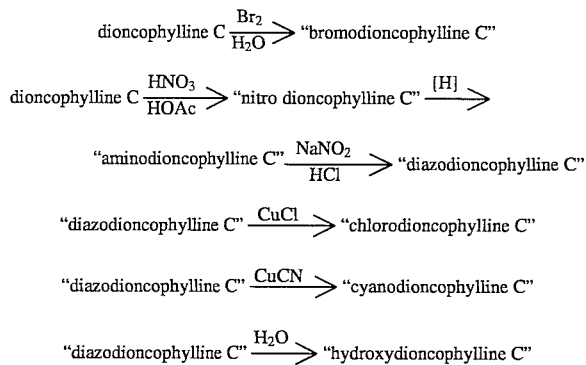

Additionally, the following new modifications are disclosed herein:

1. Substitution of one or more hydrogen substituents on the aryl systems by acyl or $C_1$–$C_6$ alkyl.

For example, for preparation of an acyl derivative, the suitably protected (e.g., N-benzylated) naphthylisoquinoline is reacted with RCOCl and $AlCl_3$ to give a corresponding acyl derivative, which can then be deprotected (e.g., by N-debenzylation) if desired. For preparation of the corresponding alkyl naphthylisoquinoline, the acyl naphthylisoquinoline is treated with $LiAlH_4/AlCl_3$.

2. Replacement of a methyl group with a hydrogen substituent.

For example, a methyl-substituted naphthylisoquinoline may be oxidized to give a corresponding carboxyl-substituted naphthylisoquinoline, which may then be decarboxylated to give the final desired (demethylated) naphthylisoquinoline.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of preparing a monomeric naphthylisoquinoline alkaloid comprising:

(a) preparing a naphthalene building block with at least one activation group at a coupling site and, optionally, with at least one protective group as a precursor to a free hydroxyl group desired in said monomeric naphthylisoquinoline alkaloid, (b) preparing an isoquinoline building block with at least one activation group at a coupling site and, optionally, with at least one protective group as a precursor to a free hydroxyl group desired in said monomeric naphthylisoquinoline alkaloid, wherein said isoquinoline building block is a tetrahydroisoquinoline, dihydroisoquinoline, or fully aromatic isoquinoline building block, and (c) coupling said naphthalene and isoquinoline building blocks at said coupling sites to form said monomeric naphthylisoquinoline alkaloid.

2. The method of claim 1, which method further comprises:

(d) removing said protective groups from said monomeric naphthylisoquinoline alkaloid, and (e) purifying said monomeric naphthylisoquinoline alkaloid.

3. The method of claim 2, wherein said purifying comprises purifying by HPLC.

4. The method of claim 1, wherein said protective group is an isopropyl group.

5. The method of claim 1, wherein one of said activation groups is selected from the group consisting of boronic acid and trialkylstannyl groups, and the other of said activation groups is selected from the group consisting of halogen and O-triflate leaving groups.

6. The method of claim 1, wherein said coupling is effected by transition metal catalysis.

7. The method of claim 6, wherein said coupling is effected by using Pd.

8. The method of claim 1, wherein said isoquinoline building block is a tetrahydroisoquinoline building block having methyl groups at C-1 and C-3.

9. The method of claim 1, wherein said isoquinoline building block is a dihydroisoquinoline building block having a methyl group at C-3.

10. The method of claim 1, wherein said coupling of said naphthalene and isoquinoline building blocks is done by forming a C-8' to C-5 naphthalene/isoquinoline linkage.

11. The method of claim 10, wherein said activation group for said naphthalene building block is trialkylstannyl, said activation group for said isoquinoline building block is bromine, and said protective group is an isopropyl group.

12. The method of claim 2, wherein said coupling of said naphthalene and isoquinoline building blocks is done by forming a naphthalene/isoquinoline linkage other than a C-8' to C-5 naphthalene/isoquinoline linkage.

13. The method of claim 12, wherein said activation group for said naphthalene building block is trialkylstannyl or a boronic acid group, said activation group for said isoquinoline building block is a halogen or an O-triflate leaving group, and said protective group is an isopropyl group.

14. The method of claim 10, wherein said monomeric naphthylisoquinoline alkaloid has the formula

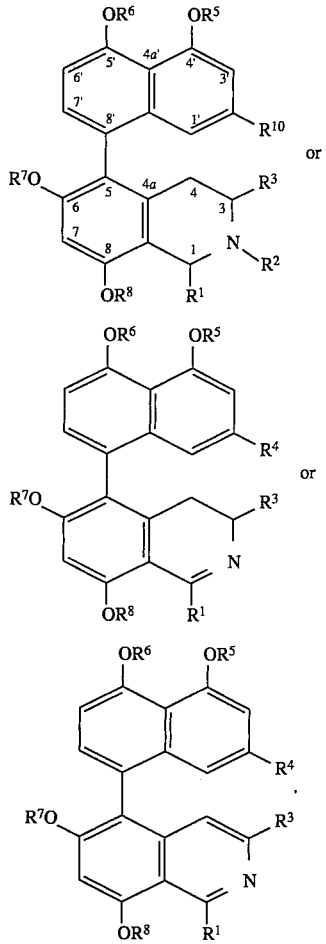

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl, or aryl and one or more of the ring positions 1, 3, 4, 1', 2', 3', 4', 5', 5', 6', 7', 6, 7, and 8 may be substituted with halo, nitro, amino, hydroxyl, thiol, acyl, $C_1$–$C_6$ alkyl, or cyano, with the proviso that $R^{10}$ is not methyl when $R^1$ and $R^3$ are methyl.

15. The method of claim 10, wherein said monomeric naphthylisoquinoline alkaloid has the formula

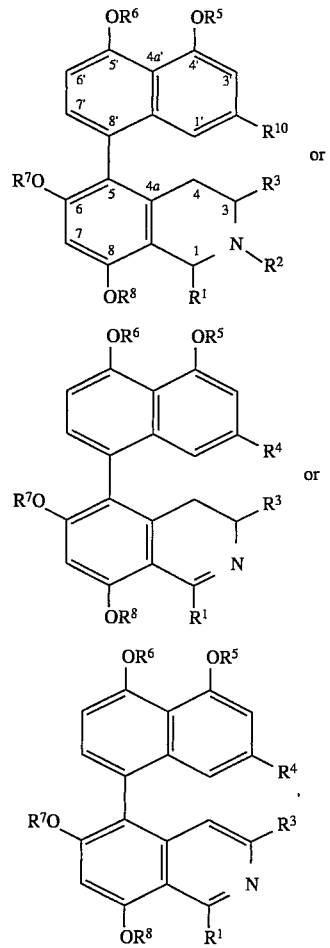

wherein (a) $R^1$, $R^3$, $R^4$, and $R^{10}$ may be the same or different and each may be H or $C_1$–$C_6$ alkyl, $R^2$, $R^5$, $R^6$, $R^7$ and $R^8$ may be the same or different and each may be H, $C_1$–$C_6$ alkyl $R^9CH_2$—, $R^9CO$—, or $R^9SO_2$—, $R^9$ may be H, $C_1$–$C_6$ alkyl or aryl and one or more of the ring positions 1, 3, 4, 1', 2', 5', 6', 6', 7', 6, 7, and 8 may be substituted with halo, nitro, amino, hydroxyl, thiol, acyl, $C_1$–$C_6$ alkyl, or cyano, (b) one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, and one or more aromatic hydrogen substituent(s) may instead be halo, nitro, amino, hydroxyl, thiol, or cyano, and (c) one or more aromatic hydrogen substituent(s) is instead an acyl or $C_1$–$C_6$ alkyl substituent.

16. The method of claim 15, wherein $R^{10}$ is not methyl when $R^1$ and $R^3$ are methyl.

17. The method of claim 12, wherein said monomeric naphthylisoquinoline alkaloid is a compound selected from the group consisting of dioncophylline B, dioncopeltine A, dioncophylline A, dioncophylline C, dioncolactone A, N-methyldioncophylline A, ancistrobrevine D, ancistrocladine, 5'-O-demethyl-8-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyldioncophylline C, wherein (a) the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, and one or more aromatic hydrogen substituent(s) may instead be halo, nitro, amino, hydroxyl, thiol, or cyano, and (b) one or more aromatic hydrogen substituent(s) is instead an acyl or $C_1$–$C_6$ alkyl substituent, at least one $CH_3$ is instead H, and/or the tetrahydroisoquinoline is instead a dihydroisoquinoline or a fully aromatic isoquinoline.

18. The method of claim 1, wherein said coupling produces a carbon-carbon bond between said naphthalene and isoquinoline building blocks.

19. The method of claim 18, wherein said monomeric naphthylisoquinoline alkaloid has the formula

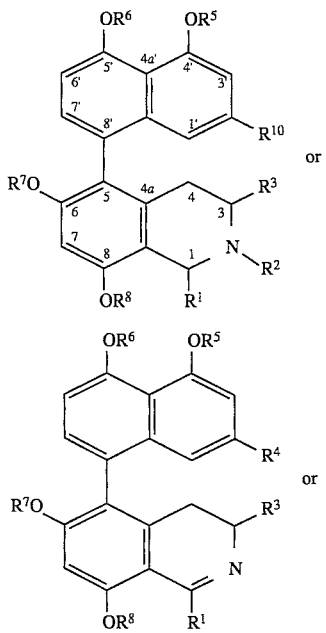

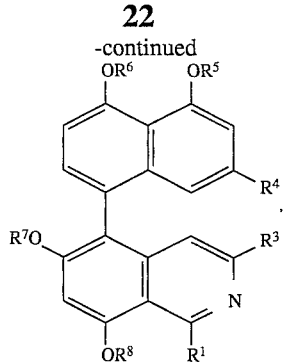

wherein $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl, or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, with the proviso that $R^{10}$ is not methyl when $R^1$ and $R^3$ are methyl.

20. The method of claim 18, wherein said monomeric naphthylisoquinoline alkaloid has the formula

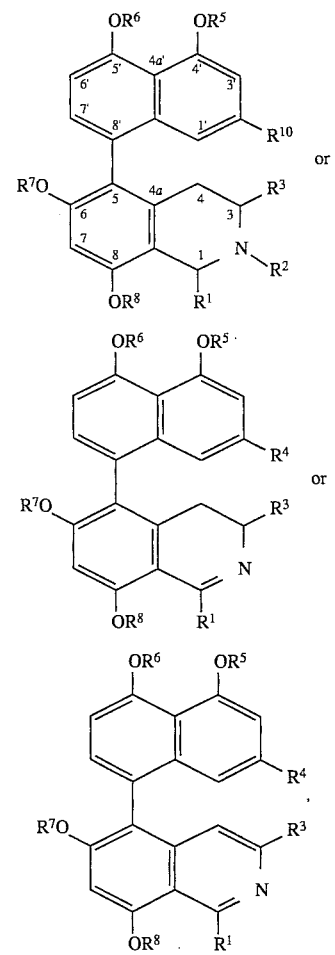

wherein (a) $R^1$, $R^3$, $R^4$, and $R^{10}$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH_2$—, $R^9CO$—, or $R^9SO_2$—, $R^9$ may be H, $C_1$–$C_6$ alkyl, or aryl, and one or more of the ring positions 1, 3, 4, 1', 2', 3', 4', 5', 6', 7', 6, 7, and 8 may be substituted with halo, nitro, amino, hydroxyl, thiol, acyl, $C_1$–$C_6$ alkyl, or cyano, (b) one or more phenolic hydroxyl group (s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, and one or more aromatic hydrogen substituent(s) may instead be halo, nitro, amino, hydroxyl, thiol, or cyano, and (c) one or more aromatic hydrogen substituent(s) is instead an acyl or $C_1$–$C_6$ alkyl substituent.

21. The method of claim 20, wherein $R^{10}$ is not methyl when $R^1$ and $R^3$ are methyl.

22. The method of claim 21, wherein said monomeric naphthylisoquinoline alkaloid is a compound selected from the group consisting of dioncophylline B, dioncopeltine A, dioncophylline A, dioncophylline C, dioncolactone A, N-methyldioncophylline A, ancistrobrevine D, ancistrocladine, 5'-O-demethyl-8-O-methyl-7-epi-dioncophylline A, 5'-O-demethyl-7-epi-dioncophylline A, dioncophylleine A, (±)-dioncophyllacine A, hamatine, ancistrobrevine A, 6-O-demethyl-ancistrobrevine A, ancistrobarterine A, 7-epi-dioncophylline A, N-formyl ancistrocladine, N-methyl-ancistrocladine, 6-deoxy-N-methylancistrocladine, N-formyl-O, O-dimethyl-dioncophylline C, N-formyl-dioncophylline C, N-formyl-8-O-benzyl-dioncophylline C, N-formyl-8-O-methyl-dioncophytline C, N-formyl-8-O-pivaloyl-dioncophylline C, N-formyl-8-O-acetyl-dioncophylline C, N-formyl-8-O-benzoyl-dioncophylline C, and 8-O-methyldioncophylline C, wherein (a) the configurations at C-1 and C-3 may instead be the same or different and each may be R or S, the coupling points comprising the naphthalene/isoquinoline axis may be different, the configuration about the axis may be different, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, and one or more secondary amine site(s) may instead be an amide, sulfonamide, tertiary amine, alkyl quaternary ammonium salt or corresponding Hoffmann elimination product thereof, one or more tertiary amine site(s) may instead be a secondary amine, and one or more aromatic hydrogen substituent(s) may instead be halo, nitro, amino, hydroxyl, thiol, or cyano, and (b) one or more aromatic hydrogen substituent(s) is instead an acyl or $C_1$–$C_6$ alkyl substituent, at least one $CH_3$ is instead H, and/or the tetrahydroisoquinoline is instead a dihydroisoquinoline or a fully aromatic isoquinoline.

* * * * *